(12) United States Patent
Shin et al.

(10) Patent No.: US 8,410,116 B2
(45) Date of Patent: Apr. 2, 2013

(54) BIS(STYRYL)PYRIMIDINE OR BIS(STYRYL)BENZENE COMPOUNDS, PHARMACEUTICALLY ACCEPTABLE SALTS THEREOF, PREPARATION METHOD THEREOF, AND PHARMACEUTICAL COMPOSITION FOR PREVENTION OR TREATMENT OF DISEASES FEATURING AMYLOIDS COMPRISING THE SAME AS AN ACTIVE INGREDIENT

(75) Inventors: Kye Jung Shin, Seoul (KR); Eun Joo Roh, Seoul (KR); Yun Suk Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 228 days.

(21) Appl. No.: 12/429,552

(22) Filed: Apr. 24, 2009

(65) Prior Publication Data
US 2010/0190803 A1    Jul. 29, 2010

(30) Foreign Application Priority Data
Jan. 23, 2009    (KR) .................. 10-2009-0006092

(51) Int. Cl.
*C07D 239/34*    (2006.01)
*A61K 31/505*    (2006.01)
(52) U.S. Cl. ........ 514/256; 544/315; 544/316; 544/318; 544/335; 514/274
(58) Field of Classification Search .................. 544/315, 544/316, 318, 335; 514/256, 274
See application file for complete search history.

(56) References Cited

U.S. PATENT DOCUMENTS

| | | | |
|---|---|---|---|
| 5,965,568 A | 10/1999 | Kakihana et al. | |
| 6,310,107 B1 | 10/2001 | Kato et al. | |
| 7,112,616 B2* | 9/2006 | Takizawa et al. | 522/8 |
| 2008/0182846 A1 | 7/2008 | Meguro et al. | |

FOREIGN PATENT DOCUMENTS
WO    2008/131059 A2    10/2008

OTHER PUBLICATIONS

Stark, CAPLUS Abstract 3:6274 (1909).*
Brown et al., CAPLUS Abstract 43:17545 (1948).*
Sakamoto et al., Studies on pyrimidine derivatives XXXVI, Chemical & Pharmaceutical Bulletin (1984), 32(5), pp. 2005-2010.*
Vanden Eynde et al., CAPLUS Abstract 136:69791 (2001).*
Mainil et al., Optical and thermal properties of novel diazine-based oligo(phenylenevinylene)s, e-Polymers (2003) Paper No. 56, pp. 1-21.*
Liu et al., Two-photon absorption of a series of V-shape molecules, Journal of Materials Chemistry (2007), 17(44), pp. 4685-4689.*
Achelle et al., V-Shaped 4,6-Bis(arylvinyl)pyrimidine Oligomers: Synthesis and Optical Properties, Journal of Organic Chemistry (2009), 74, pp. 3711-3717 (Published on Web Apr. 21, 2009).*
Li et al., Facile Synthesis and Systematic Investigations of a series of Novel Bent Shaped Two-Photon Absorption Chromophores Based on Pyrimidine, Chem. Asian J. (2009), 4, pp. 668-680 (Published online: Mar. 31, 2009).*
Massoud et al., Update on the Pharmacological Treatment of Alzheimer's Disease, Current Neuropharmacology, 2010, 8, pp. 69-80.*
Damasio, Alzheimer's disease and related dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Jean Jacques Vanden Eyndea, et al. Synthetic Communications, 31(20), 3167-3173, Sep. 30, 2001 online publication.

* cited by examiner

*Primary Examiner* — Deepak Rao
(74) *Attorney, Agent, or Firm* — Ladas & Parry LLP

(57) ABSTRACT

Disclosed are bis(styryl)pyrimidine or bis(styryl)benzene compounds, represented by Chemical Formula 1, pharmaceutically acceptable salts, a method for preparing the same, and a pharmaceutical composition for the prevention and treatment of amyloidosis-associated diseases, comprising the same as an active ingredient. Having the ability to inhibit the deposition of beta amyloid and to reduce the toxicity of beta amyloid, the derivatives can improve learning and memory and can be useful in the prevention and treatment of amyloidosis-associated diseases.

[Chemical Formula 1]

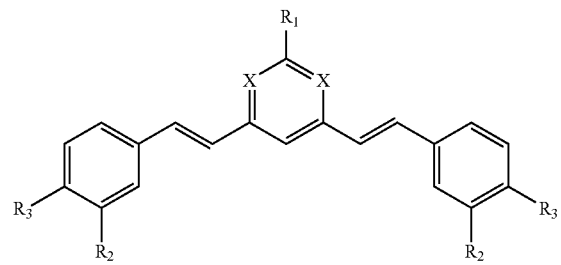

(wherein $R_1$, $R_2$, $R_3$ and X are as defined in the specification).

15 Claims, 12 Drawing Sheets

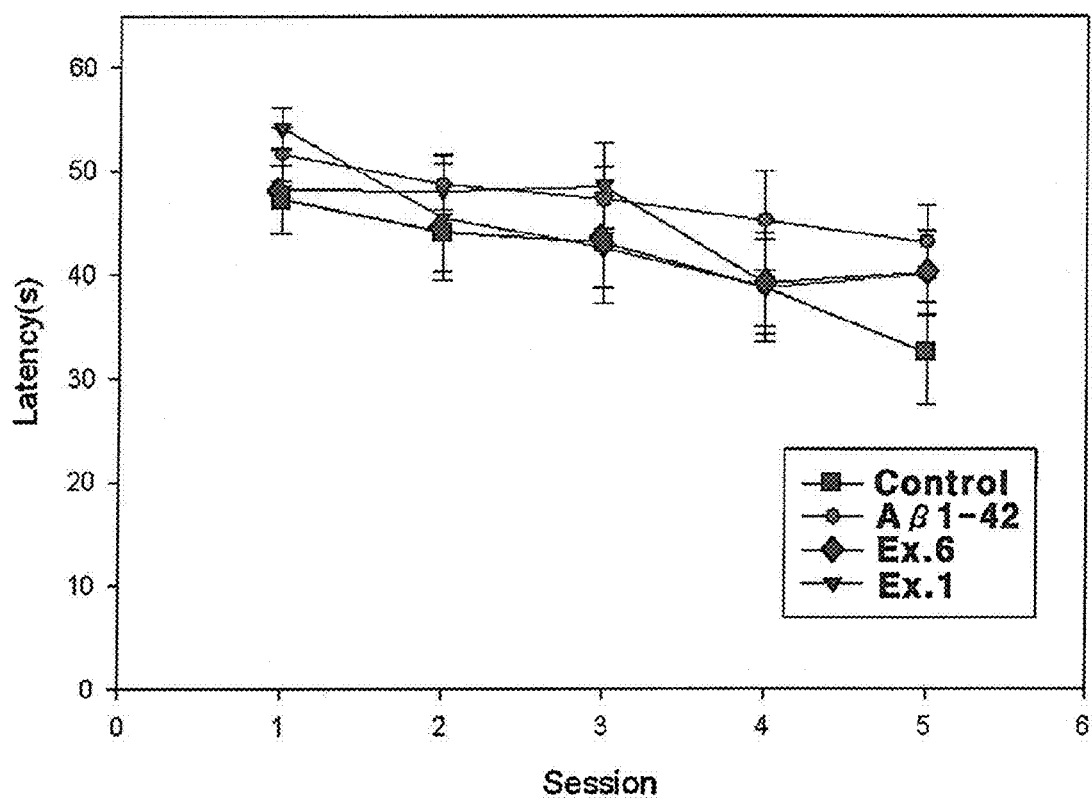

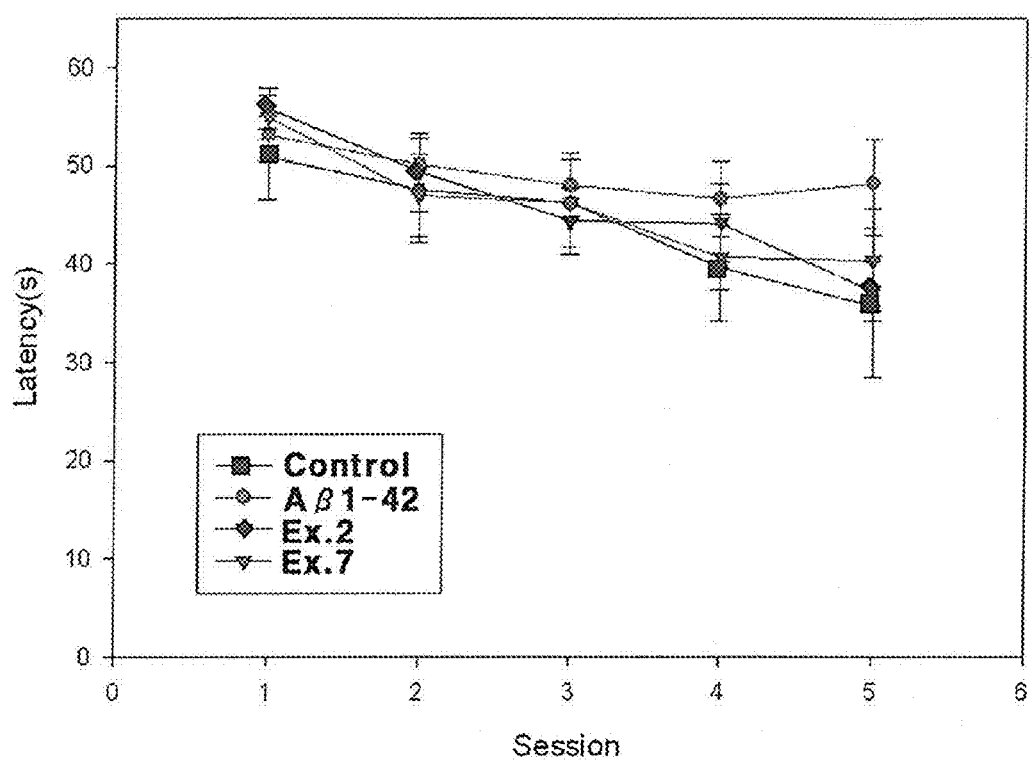

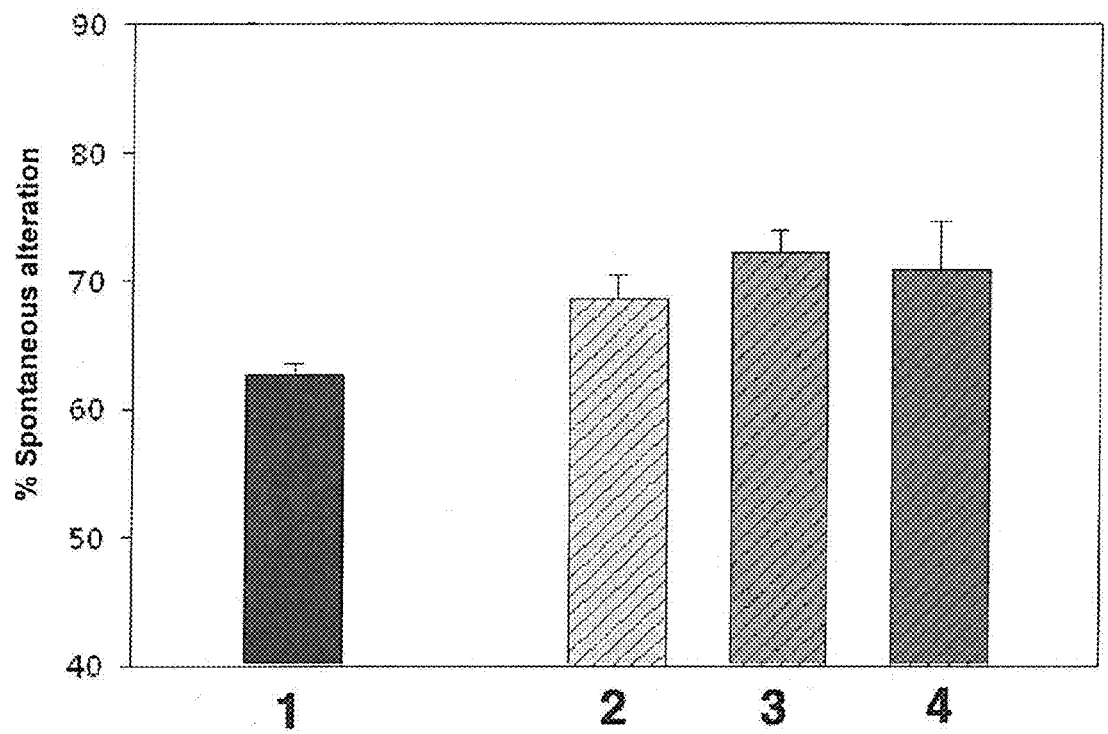

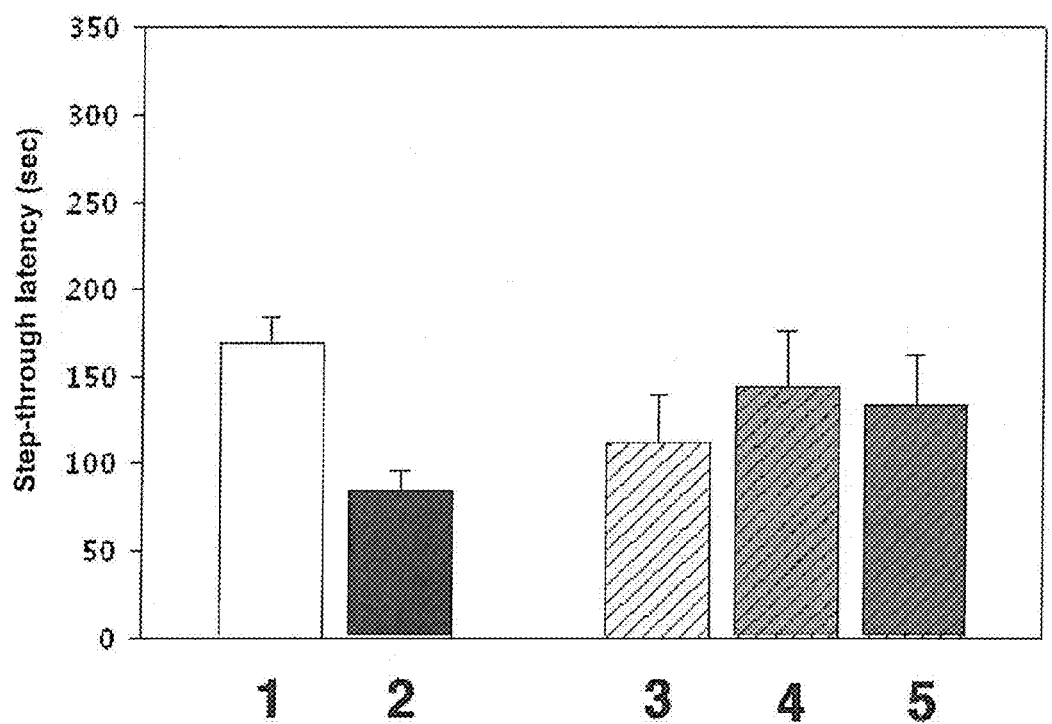

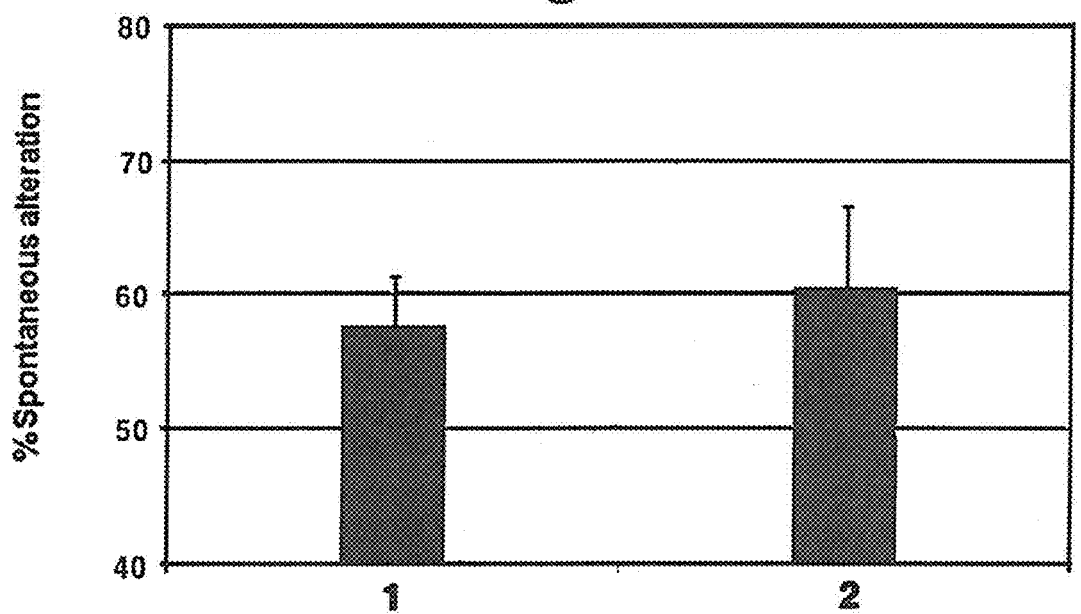

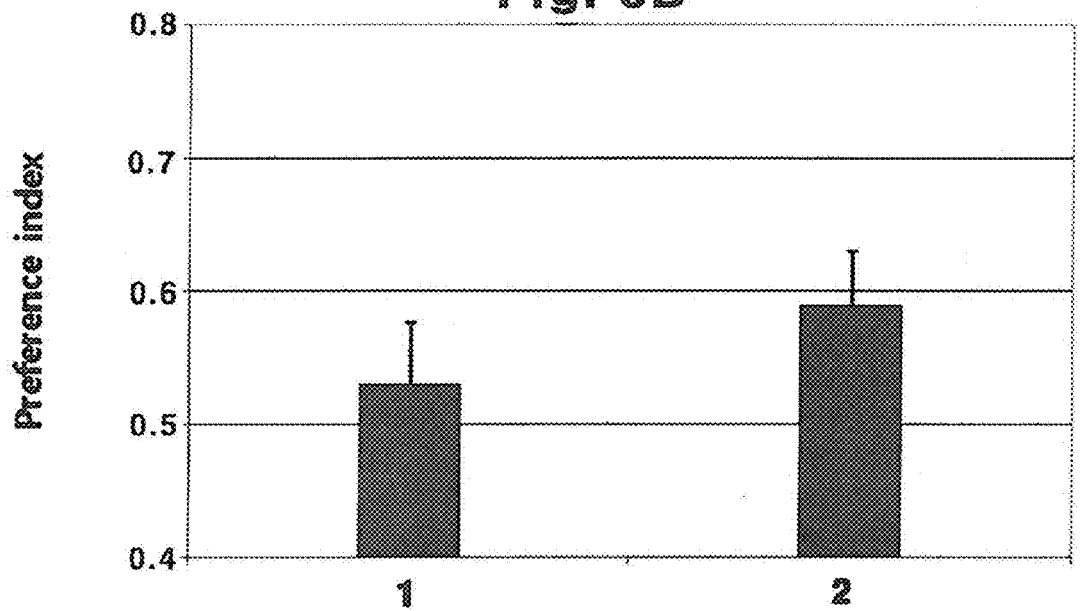

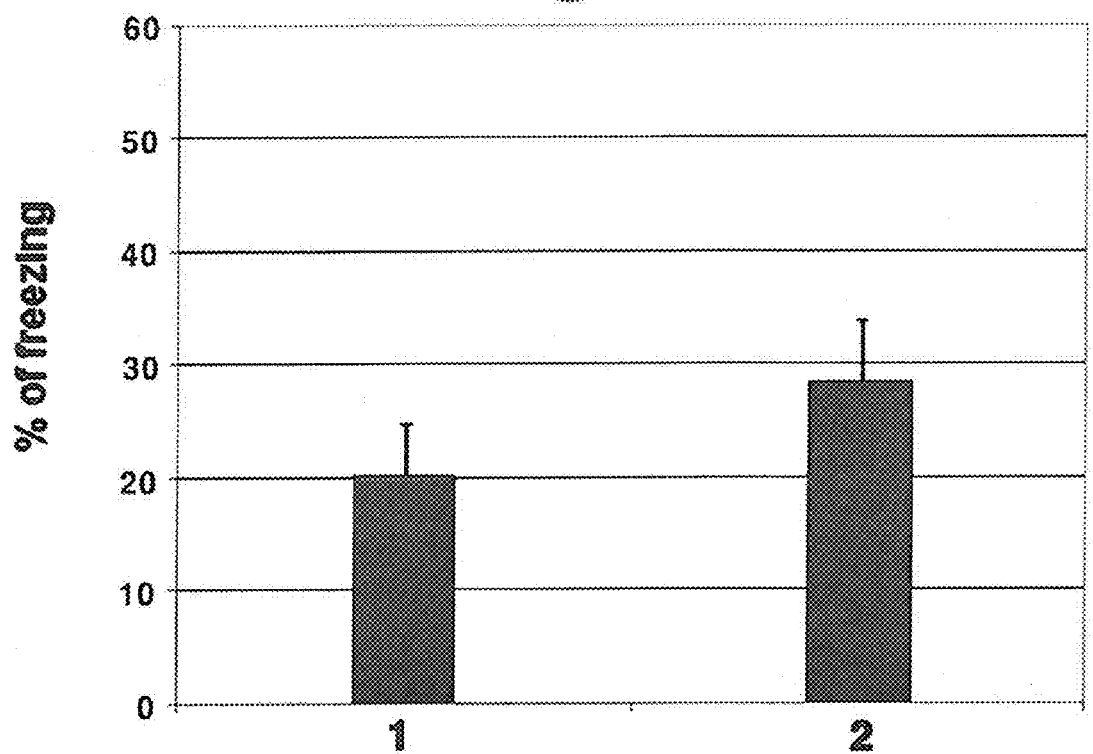

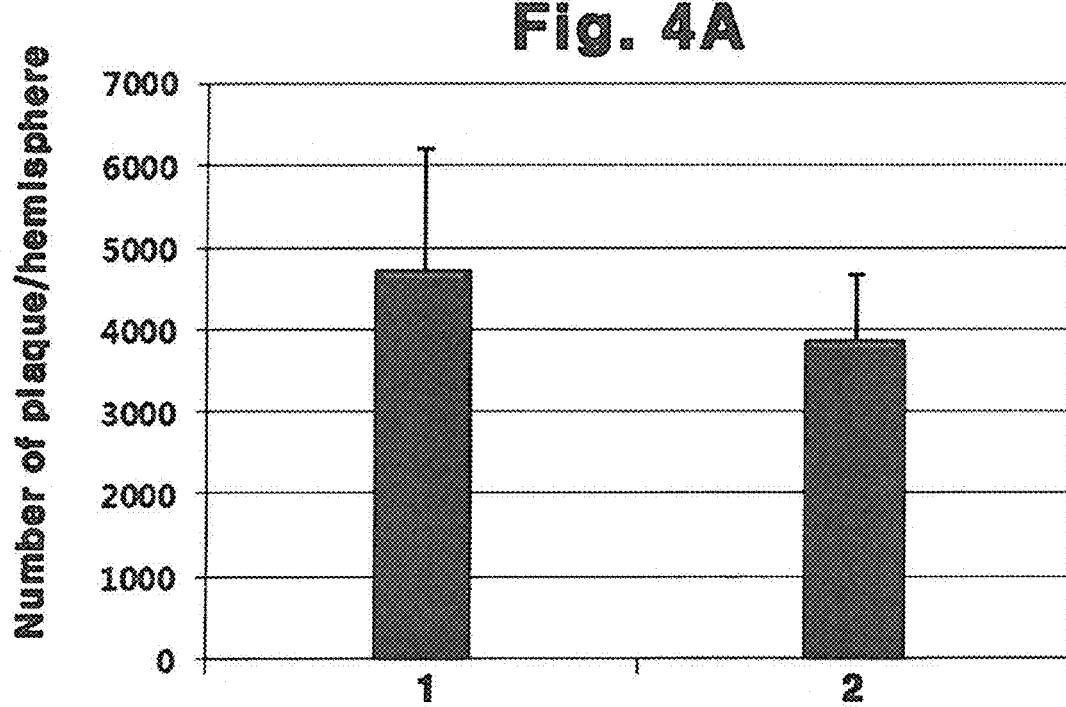

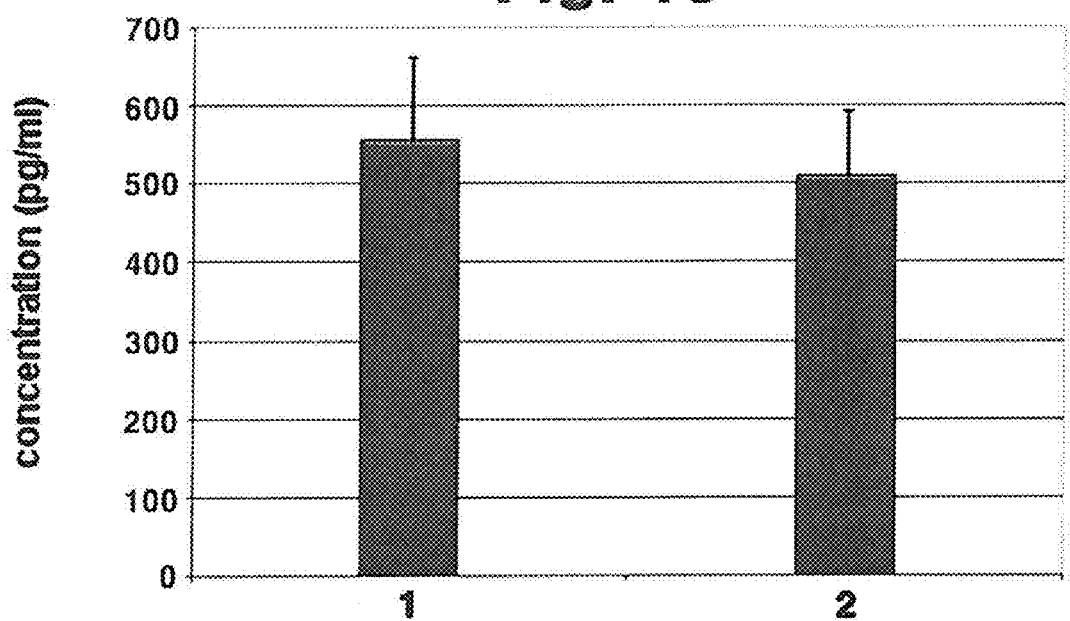

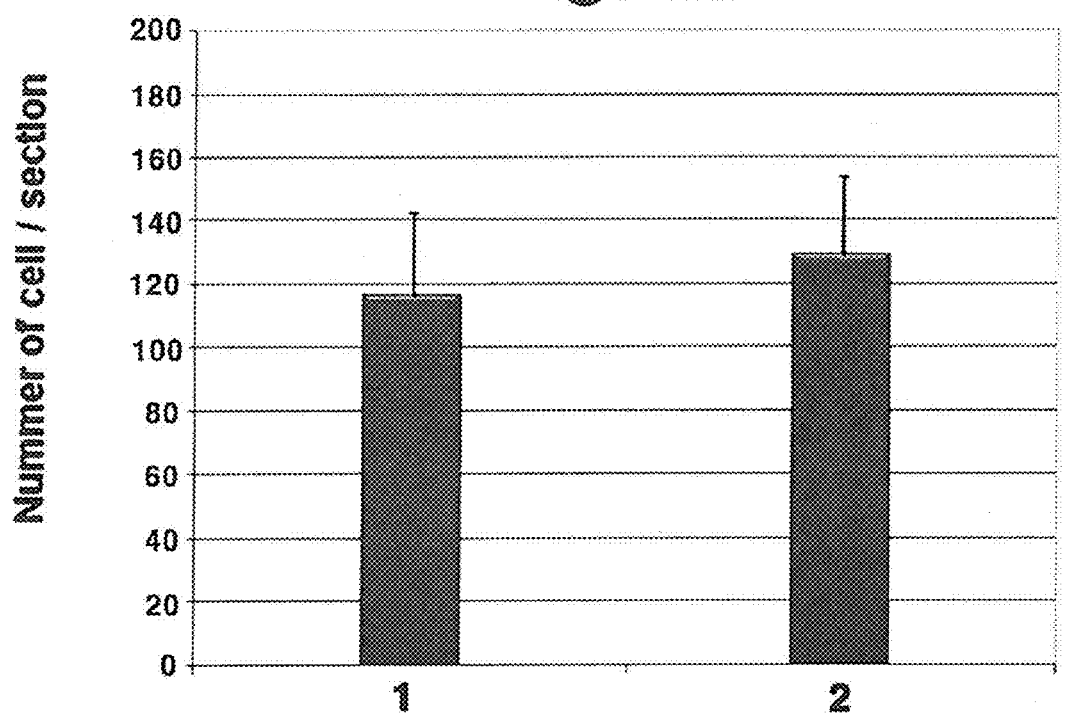

US 8,410,116 B2

BIS(STYRYL)PYRIMIDINE OR BIS(STYRYL)BENZENE COMPOUNDS, PHARMACEUTICALLY ACCEPTABLE SALTS THEREOF, PREPARATION METHOD THEREOF, AND PHARMACEUTICAL COMPOSITION FOR PREVENTION OR TREATMENT OF DISEASES FEATURING AMYLOIDS COMPRISING THE SAME AS AN ACTIVE INGREDIENT

CROSS-REFERENCES TO RELATED APPLICATION

This patent application claims the benefit of priority under 35 U.S.C. §119 of Korean Patent Application No. 10-2009-0006092 filed on Jan. 23, 2009, the contents of which are incorporated herein by reference.

BACKGROUND OF THE INVENTION

1. Field of the Invention

The present invention relates to bis(styryl)pyrimidine or bis(styryl)benzene compounds, pharmaceutically acceptable salts thereof, a method for the preparation thereof, and a pharmaceutical composition for the prevention and treatment of diseases associated with beta-amyloid deposition, that is, amyloidosis-associated diseases.

2. Description of the Related Art

With the increase in the average longevity of human beings all over the world and the entry into an aging society, there has been a great increase in the incidence of degenerative brain disorders such as senile dementia including Alzheimer's disease, apoplexy, Parkinson's disease, etc. Reports from the Korea Institute for Health and Social Affairs discloses that the number of senile persons was about 7% of the total population in 2000, the beginning stage of the aging society in Korea, and this increased to 3.97 million in 2003 with a population ratio of 8.3%, and will amount to about 14.4% in 2019 with the entry of Korea into an aged society. In Korea, dementia is reported in about 15% of senile adults in the ages of 75 to 79 and in as many as about 39% of adults of more than 80 years of age. Females are known to have a twice or three times higher rate of incidence of dementia than do males.

Dementia is a generic term for a set of symptoms accompanying an abnormal decline in the general cognitive functions of language, learning and memory and higher mental functions as a result of the injury or destruction of a normally developed brain by external factors such as postnatal damage or disease. Progressive memory impairment is accompanied by behavior impairments such as disorientation in language, person and place, incurring social and occupational impairments. Dementia is caused largely by Alzheimer's disease, vascular dementia, particular cerebral diseases and systemic diseases with over 50% of the cases resulting from Alzheimer's disease.

Alzheimer's disease is anatomically characterized by the decline and loss of neurons responsible for memory and cognition. The pathophysiological features of Alzheimer's disease are associated with both senile plaque and neurofibrillary tangles in the brain. Research indicates that the pathological features of Alzheimer's disease are associated with both amyloid plaque and neurofibrillary tangles in the brain. Among various causes including immunological factors, genetic factors, viral infection, environmental factors such as toxic compounds, damage to the brain, etc., the deposition of beta-amyloid protein and the formation of neurofibrillary tangles are known to play the most important roles in the incidence of Alzheimer's disease. Amyloid plaque results from the deposition of amyloid-beta peptide, and neurofibrillary tangles are pathological protein aggregates formed by hyperphosphorylation of a microtubule-associated protein known as tau, causing it to aggregate in an insoluble form which leads to neurodegeneration.

Beta amyloid is a peptide of 40 amino acids (beta amyloid 1-40) or 42 amino acids (beta amyloid 1-42) that appear to be the main constituent of amyloid plaque in the brains of Alzheimer's disease patients. Beta amyloid is formed after sequential cleavage of the amyloid precursor protein by β and γ secretases. Beta amyloid fibril formation, which is known to have direct influence on the formation of plaque, occurs via a complex multi-step nucleated polymerization mechanism that involves discrete soluble oligomeric intermediates termed protofibrils, which disappear upon fibril formation. Recent studies have reported that the oligomers are more potential in neurotoxicity than are fibrils, thus making the prevention or inhibition of oligomer formation an attractive therapy for Alzheimer's disease.

Most of the therapeutic agents developed so far have been cholinergic drugs which are designed to increase the level of acetylcholine in the brain or the activity of cholinergic neurons on the basis of the fact that acetylcholine levels in the brains of Alzheimer's disease patients are lower than in those of healthy persons. Currently available cholinergic drugs, such as Donepezil, Rivastigmin, Galantamine, Memantine, etc., however, aim to improve memory impairment only, with limitations to the fundamental medical treatment of Alzheimer's disease and the production of side effects.

Leading to the present invention, intensive and thorough research into therapies for Alzheimer's disease, conducted by the present inventors, resulted in the finding that novel bis(styryl)pyrimidine or bis(styryl)benzene compounds inhibit the deposition of beta amyloid and reduce the toxicity of beta amyloid, thus being useful in the treatment of diseases featuring amyloids, such as Alzheimer's disease.

SUMMARY OF THE INVENTION

It is therefore an object of the present invention to provide a novel bis(styryl)pyrimidine or bis(styryl)benzene compound and a pharmaceutically acceptable salt thereof.

It is another object of the present invention to provide a method for preparing the novel derivative.

It is a further object of the present invention to provide a pharmaceutical composition for the prevention and treatment of diseases resulting from the deposition of beta amyloid, comprising the novel derivative as an active ingredient.

In accordance with an aspect thereof, the present invention provides a bis(styryl)pyrimidine or bis(styryl)benzene compound, represented by the following Chemical Formula 1, a pharmaceutically acceptable salt thereof, and a method for the preparation thereof:

[Chemical Formula 1]

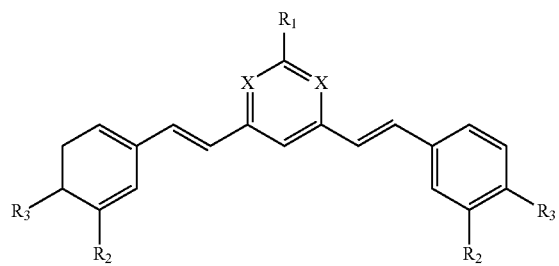

(wherein, $R_1$, $R_2$, $R_3$ and X are as defined in the specification).

In accordance with another aspect thereof, the present invention provide a pharmaceutical composition for the prevention and treatment of amyloidosis-associated diseases, comprising as an active ingredient a bis(styryl)pyrimidine or bis(styryl)benzene compound, represented by Chemical Formula 1, showing ability to inhibit the cerebral deposition of beta amyloid and to alleviate the toxicity of beta amyloid aggregates.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows results of the water maze task designed to test mice for spatial learning ability in graphs, in accordance with Test Example 4;

FIG. 3 shows results of conducting Y-maze, cognitive performance and context fear conditioning tasks with the transgenic mice of Test Example 5, these being designed to test learning and memory abilities upon treatment with the compound of the present invention ((A): Y-maze, (B): cognitive performance, (C): context fear conditioning: control (1); Cpd of Example 1 (2))

DESCRIPTION OF THE PREFERRED EMBODIMENTS

Figure 2B:
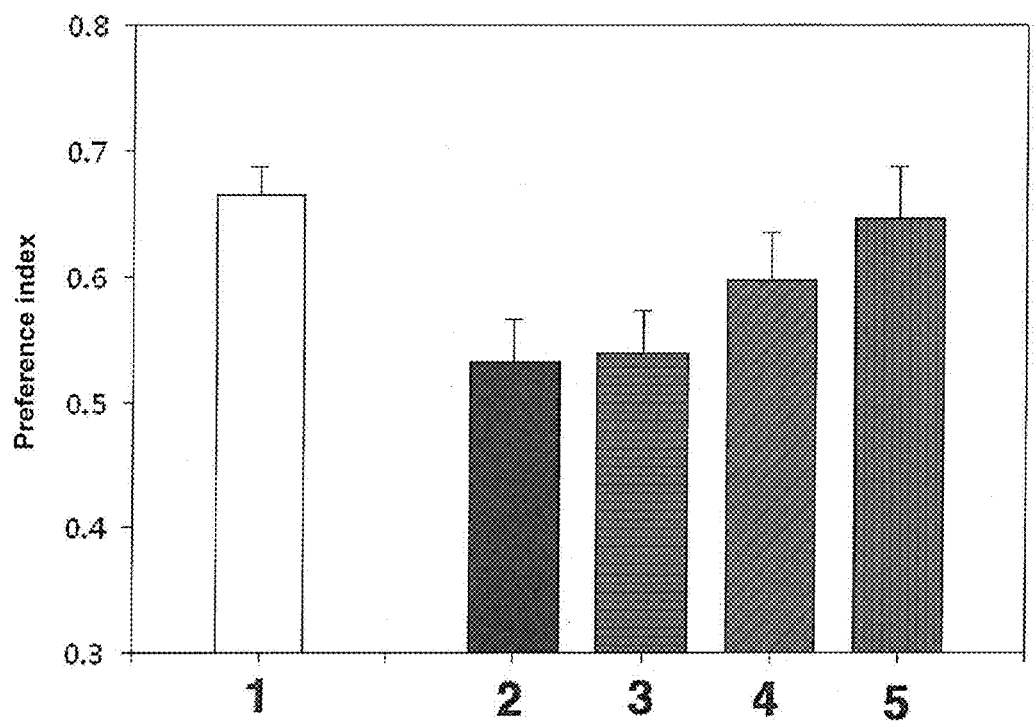
FIG. 2 shows results of Y-maze, cognitive performance, and passive avoidance tasks with acute AD models of Test Example 4, these being designed to test learning and memory abilities upon treatment with the compound of the present invention ((A) Y-maze: Aβ1-42 10 nM (1); Aβ1-42 10 nM+Cpd. of Example 1 50 mg/kg. p.o. (2); Aβ1-42 10 nM+Cpd. of Example 1 100 mg/kg. p.o. (3); Aβ1-42 10 nM+Cpd. of Example 1 200 mg/kg. p. o. (4); (B) Cognitive performance: control (1); Aβ1-42 10 nM (2); Aβ1-42 10 nM+Cpd. of Example 1 50 mg/kg. p.o. (3); Aβ1-42 10 nM+Cpd. of Example 1 100 mg/kg. p.o. (4); Aβ1-42 10 nM+Cpd. of Example 1 200 mg/kg. p.o. (4); (C) passive avoidance: control (1); Aβ1-42 10 nM (2); Aβ1-42 10 nM+Cpd. of Example 1 50 mg/kg. p.o. (3); Aβ1-42 10 nM+Cpd. of Example 1 100 mg/kg. p.o. (4); Aβ1-42 10 nM+Cpd. of Example 1 200 mg/kg. p.o. (5))

In accordance with an aspect thereof, the present invention pertains to bis(styryl)pyrimidine or bis(styryl)benzene compounds, represented by the following Chemical Formula 1, or pharmaceutically acceptable salts thereof.

[Chemical Formula 1]

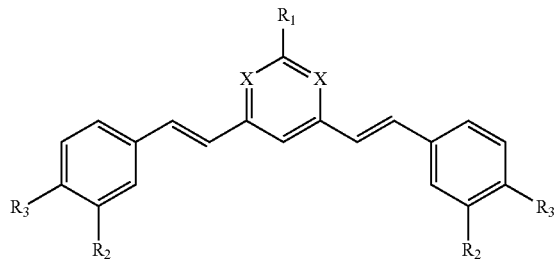

In Chemical Formula 1,
X is independently nitrogen or carbon;
$R_1$ is selected from the group consisting of hydrogen, hydroxy, alkoxy of $C_1$~$C_4$ and alkylthio of $C_1$~$C_4$; and
$R_2$ and $R_3$ are independently selected from hydrogen, hydroxy, alkoxy of $C_1$~$C_4$ and di($C_1$~$C_4$)alkylamino.

Preferable are derivatives of Chemical Formula 1 in which,
X is independently nitrogen or carbon;
$R_1$ is selected from the group consisting of hydrogen, hydroxy, methoxy, ethoxy, methylthio and ethylthio; and
$R_2$ and $R_3$ are independently selected from the group consisting of hydrogen, hydroxy, methoxy, ethoxy, dimethylamino and diethylamino.

More preferably, the compound of Formula 1 according to the present invention is selected from the group consisting of:
(1) (E,E)-4,6-bis(3'-hydroxy-4'-methoxystyryl)pyrimidine;
(2) (E,E)-4,6-bis[4'-hydroxy-3'-(N,N-dimethylamino)styryl]pyrimidine;
(3) (E,E)-1,3-bis(3'-hydroxy-4'-methoxystyryl)benzene;
(4) (E,E)-4,6-bis(4'-hydroxystyryl)pyrimidine;
(5) (E,E)-4,6-bis(3'-hydroxystyryl)pyrimidine;
(6) (E,E)-4,6-bis(4'-hydroxy-3'-methoxystyryl)pyrimidine;
(7) (E,E)-4,6-bis[3'-hydroxy-4'-(N,N-dimethylamino)styryl]pyrimidine;
(8) 2-methoxy-(E,E)-4,6-bis(4'-hydroxystyryl)pyrimidine;
(9) 2-methoxy-(E,E)-4,6-bis(3'-hydroxystyryl)pyrimidine;
(10) 2-methoxy-(E,E)-4,6-bis(4'-hydroxy-3'-methoxystyryl)pyrimidine;
(11) 2-methoxy-(E,E)-4,6-bis(3'-hydroxy-4'-methoxystyryl)pyrimidine;
(12) 2-methoxy-(E,E)-4,6-bis[4'-hydroxy-3'-(N,N-dimethylamino)styryl]pyrimidine;
(13) 2-methoxy-(E,E)-4,6-bis[3'-hydroxy-4'-(N,N-dimethylamino)styryl]pyrimidine;
(14) 2-methylthio-(E,E)-4,6-bis(4'-hydroxystyryl)pyrimidine;
(15) 2-methylthio-(E,E)-4,6-bis(3'-hydroxystyryl)pyrimidine;
(16) 2-methylthio-(E,E)-4,6-bis(4'-hydroxy-3'-methoxystyryl)pyrimidine;
(17) 2-methylthio-(E,E)-4,6-bis(3'-hydroxy-4'-methoxystyryl)pyrimidine;
(18) 2-methylthio-(E,E)-4,6-bis[4'-hydroxy-3'-(N,N-dimethylamino)styryl]pyrimidine;
(19) 2-methylthio-(E,E)-4,6-bis[3'-hydroxy-4'-(N,N-dimethylamino)styryl]pyrimidine;
(20) (E,E)-1,3-bis[4'-hydroxy-3'-(N,N-dimethylamino)styryl]benzene;
(21) (E,E)-1,3-bis[3'-hydroxy-4'-(N,N-dimethylamino)styryl]benzene;
(22) (E,E)-3,5-bis(4'-hydroxystyryl)phenol;
(23) (E,E)-3,5-bis(3'-hydroxystyryl)phenol;
(24) (E,E)-3,5-bis(4'-hydroxy-3'-methoxystyryl)phenol;

(25) (E,E)-3,5-bis(3'-hydroxy-4'-methoxystyryl)phenol;
(26) (E,E)-3,5-bis[4'-hydroxy-3'-(N,N-dimethylamino) styryl]phenol; and
(27) (E,E)-3,5-bis[3'-hydroxy-4'-(N,N-dimethylamino) styryl]phenol.

It should be appreciated that not only the bis(styryl)pyrimidine or bis(styryl)benzene compounds represented by Chemical Formula 1, and the pharmaceutically acceptable salts thereof, but also isomers, solvates and hydrates thereof are included within the scope of the present invention.

In accordance with another aspect thereof, the present invention pertains to a method for preparing the derivative represented by Chemical Formula 1, which is in detail described as follows.

Preparation Method 1:

The derivative of Chemical Formula 1 in accordance with the present invention, wherein X is nitrogen and described as Chemical Formula 1a in the following Reaction Scheme 1, may be prepared, as illustrated in the following Reaction Scheme 1, by a method comprising:

(1) preparing a compound of Chemical Formula 4 by condensating, a pyrimidine compound of Chemical Formula 2 with a benzaldehyde compound of Chemical Formula 3 in an alkaline condition (Step 1); and (2) deprotecting of the compound of Chemical Formula 4 (Step 2).

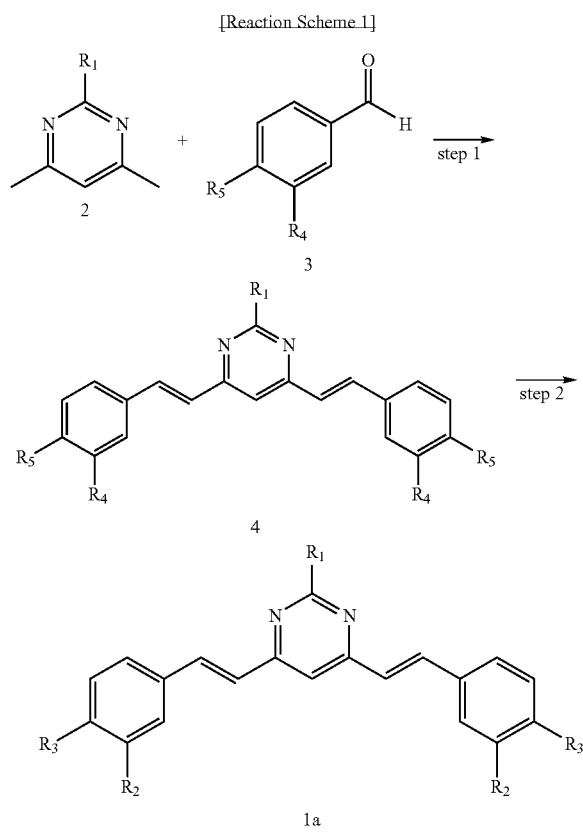

[Reaction Scheme 1]

(wherein, $R_1$, $R_2$ and $R_3$ are as defined in Chemical Formula 1; $R_4$ and $R_5$ are respectively the same as $R_2$ and $R_3$, provided that they are independently p-methoxybenzyl or methoxymethyl when $R_2$ and $R_3$ are independently hydroxyl; and the compound of Chemical Formula 1a is one derivative of Chemical Formula 1).

A detailed delineation is given of the preparation method 1, below.

In step 1 of Preparation Method 1 in accordance with the present invention, the pyrimidine-based compound 4,6-dimethylpyrimidine of Chemical Formula 2 is condensed with the benzaldehyde compound of Chemical Formula 3. This condensation is performed by refluxing a solution of the 4,6-dimethylpyrimidine compound (Chemical Formula 2) and the benzaldehyde compound (Chemical Formula 3) in the presence of a phase transfer catalyst (PTC) in an alkaline solution. The PTC can be used tetrabutylammonium hydrogen sulphate ($Bu_4NHSO_4$), benzyltrimethylammonium, etc. An aqueous sodium hydroxide solution is preferably used as an alkaline solution. Preferably, the benzaldehyde compound of Chemical Formula 3 is selected from the group consisting of the following compounds in which the hydroxyl group is protected:

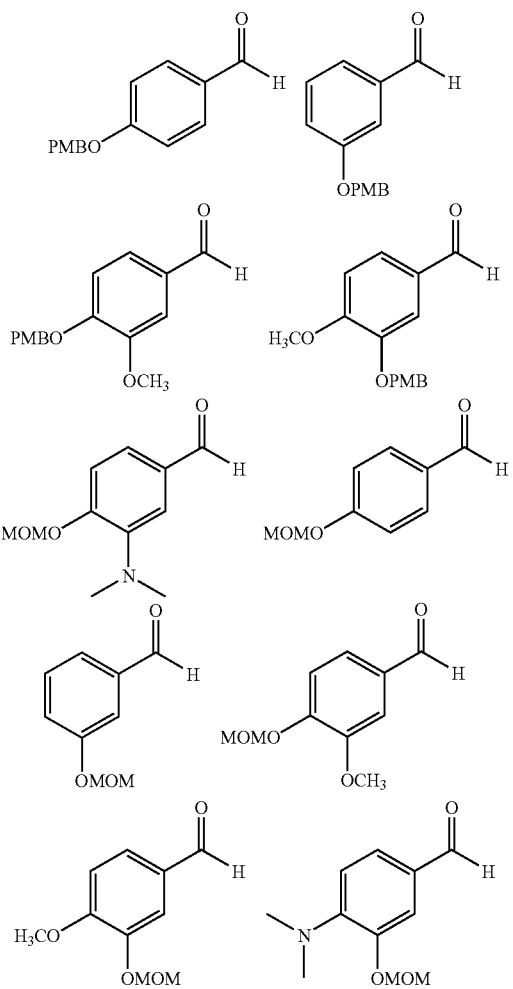

(wherein, PMB is p-methoxybenzyl and MOM is methoxymethyl)

Step 2 of Preparation Method 1 in accordance with the present invention is to deprotect the compound 4 resulting from the condensation of the step 1. The protecting group may be removed by heating in a HCl/ethanol (3:1) solvent under reflux or by stirring in a methylene chloride solvent in the presence of trifluoroacetic acid.

Preparation Method 2:

The derivative of Chemical Formula 1 in accordance with the present invention may be prepared, wherein X is carbon and described as Chemical Formula 1b in the following Reaction Scheme 2, as illustrated in the following Reaction Scheme 2, by a method comprising:

(A) reacting a benzene compound of Chemical Formula 5 with a benzaldehyde compound of Chemical Formula 3 in an ether-based organic solvent added a base at 0° C. to afford a compound of Chemical Formula 6; and (B) deprotecting the compound of Chemical Formula 6.

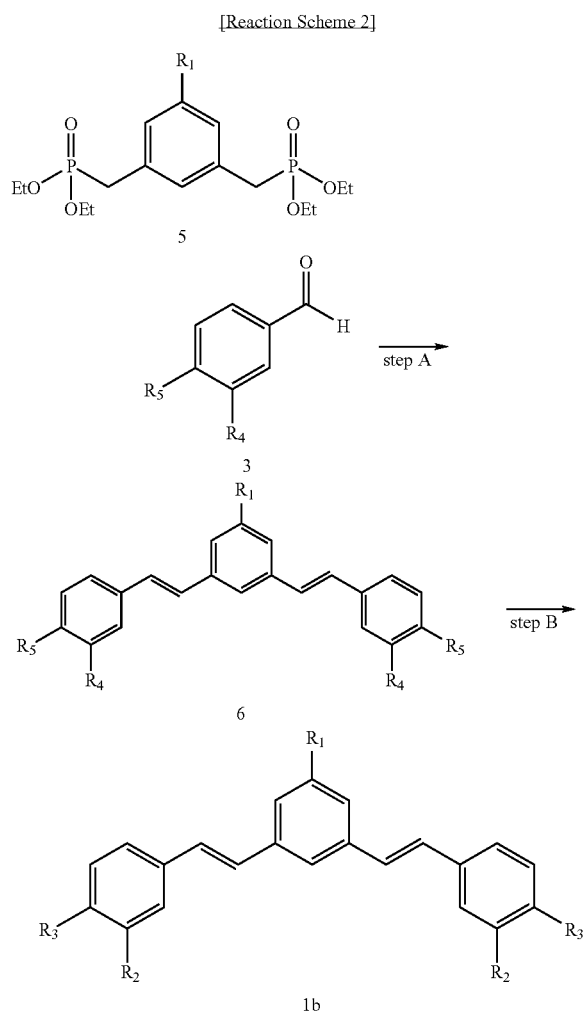

[Reaction Scheme 2]

(wherein, $R_1$, $R_2$ and $R_3$ are as defined in Chemical Formula 1; $R_4$ and $R_5$ are respectively the same as $R_2$ and $R_3$, provided that they are independently p-methoxybenzyl or methoxymethyl when $R_2$ and $R_3$ are independently hydroxyl; and the compound of Chemical Formula 1b is one of the derivatives of Chemical Formula 1).

A detailed delineation is stepwise given of the preparation method 2, below.

In step A, the Horner-Emmons olefination of 1,3-bis(diethylphosphonomethyl)benzene or 3,5-bis(diethylphosphonomethyl)phenol of Chemical Formula 5 is performed with a benzaldehyde compound of Chemical Formula 3. For this reaction, a base is added at 0° C. to a solution of 1,3-Bis (diethylphosphonomethyl)benzene or 3,5-bis(diethylphosphonomethyl)phenol and the benzaldehyde of Chemical Formula 3 in anhydrous tetrahydrofuran. Examples of the base useful in the step A include metal hydride, metal alkoxide, alkyl alkaline metal hydride or amide-formed alkaline metal hydride. Preferably, the base useful in the step A include alkaline metal hydride such as sodium hydride (NaH), lithium hydride (LiH), potassium hydride (KH), etc., and metal alkoxide such as sodium methoxide, sodium ethoxide, sodium propoxide, sodium t-butoxide, potassium t-butoxide, potassium isopropoxide, and lithium isopropoxide, with higher preference for potassium t-butoxide. Preferably, the benzaldehyde compound of Chemical Formula 3 is the same as is used in Preparation Method 1 in which the hydroxyl group is protected.

Step B of Preparation Method 2 in accordance with the present invention is to deprotect the compound 6 resulting from the olefination of the step A. The protecting group may be removed by heating in an HCl/ethanol (3:1) solvent under reflux or by stirring in a methylene chloride solvent in the presence of trifluoroacetic acid.

In accordance with a further aspect thereof, the present invention pertains to a pharmaceutical composition for the prevention and treatment of an amyloidosis-associated disease (disease caused by the deposition of beta amyloid), comprising the derivative of Chemical Formula 1 or a pharmaceutically acceptable salt thereof as an active ingredient.

Examples of the amyloidosis-associated disease include dementia, Alzheimer's disease, Down's syndrome, amyloid angiopathy, cerebral amyloid angiopathy, systemic amyloidosis and Dutch type.

The derivative of Chemical Formula 1 in accordance with the present invention was found to have excellent inhibitory activity against the formation of beta amyloid (1-42) fibrils as measured by a ThT fluorescence assay in which low fluorescence intensity was detected as compared to a control (Experimental Example 1).

In a cytotoxicity assay with HT-22 cells, most of the compounds of Chemical Formula 1 in accordance with the present invention were measured to ensure 70% or higher cell survival (Experimental Example 2).

Further, the derivatives of Chemical Formula 1 in accordance with the present invention can effectively reduce the cytotoxicity of beta amyloid as proved by high cell survival rates compared to those of the control beta amyloid (Aβ 23-35) (Experimental Example 3).

In addition, the derivatives of Chemical Formula 1 in accordance with the present invention are found to exhibit improvements in memory and cognitive performance with statistical significance, as measured by the Y-maze task, cognitive performance, passive avoidance task, and water maze task in acute Alzheimer's disease mice injected with beta amyloid (1-42) (refer to Test Example 4, Table 6 and FIGS. 1 and 2).

Further, the derivatives of Chemical Formula 1 in accordance with the present invention are found to alleviate memory impairment as measured by the Y-maze task and cognitive performance tests using the transgenic mice (refer to Test Example 5, and FIGS. 3A and 3B). It is also apparent from the data of context fear conditioning that the compounds of the present invention reduce the hippocampal damage caused by beta amyloid (refer to Test Example 5 and FIG. 3C).

Also, the compounds of Chemical Formula 1 reduce the levels of amyloid plaque and beta amyloid in the cerebral cortex and the hippocampus and increase the neuronal cell count, as compared to the control (refer to Test Example 6 and FIGS. 4A, 4B, 4C, and 4D).

Having inhibitory activity against the deposition of beta amyloid, therefore, the derivative of Chemical Formula 1 in accordance with the present invention may be useful in the prevention and treatment of amyloidosis-associated diseases.

In accordance with still a further aspect thereof, the present invention pertains to a method for treatment of amyloidosis-associated diseases, comprising administering the derivative of Chemical Formula 1 or a pharmaceutically acceptable salt thereof in a therapeutically effective amount to a subject in need thereof.

The derivative of Chemical Formula 1 or a pharmaceutically acceptable salt thereof useful in the prevention and treatment of amyloidosis-associated diseases may be formulated into any of the following, illustrative, non-limiting oral or non-oral dosage forms.

Examples of the oral dosage forms formulated with the therapeutically active agent of the present invention include tablets, pills, boluses, hard/soft capsules, liquids, suspensions, emulsions, syrups, granules, and elixirs. These dosage forms generally contain at least one diluent or excipient such as a filler, a thickening agent, a wetting agent, an disintegrant, a lubricant, a binder and a surfactant. Agar, starch, alginic acid or sodium salt thereof, or anhydrous potassium monohydrogen phosphate is useful as a disintegrant. Silica, talc, stearic acid or magnesium or calcium salts thereof, polyethylene glycol and the like are exemplified for lubricants. Magnesium aluminium silicate, starch paste, gelatin, tragacanth, methylcellulose, sodium carboxymethylcellulose, polyvinylpyrrolidine, or low-substituted hydroxylpropylcellulose may be used as a binder. Additionally, lactose, dextrose, sucrose, mannitol, sorbitol, cellulose, or glycin may be used as a diluent. If necessary, effervescent mixture, absorbents, colorants, flavorants, and/or sweetening agents, etc. may be used in combination with the additives.

For the prevention and treatment of neurodegenerative diseases, the pharmaceutical composition comprising the derivative of Chemical Formula 1 or a pharmaceutically acceptable salt thereof as an active ingredient may be administered via non-oral routes. Non-oral administration may be subcutaneous, intravenous, intramuscular, or intrathoracic injection. For use in non-oral administration, injections may be prepared by mixing the composition of the present invention with a stabilizer or buffer in water to give solutions or suspensions which are packaged in unit dosages such as ampules or vials.

The composition of the present invention may be sterilized or may contain an auxiliary agent such as a preservative, a stabilizer, a wettable powder or emulsion promoter, a osmotic pressure-regulating salt, a buffer, etc., and/or a therapeutically useful agent.

When the pharmaceutical composition for the prevention and treatment of neurodegenerative diseases, comprising the derivative of Chemical Formula 1 or a pharmaceutically acceptable salt thereof as an active ingredient in accordance with the present invention is formulated into unit doses, the active ingredient is preferably administered at a dose of from 0.1 to 1,500 mg a day for an adult weighing 70 kg. Depending on the conditions of patients, including age, body weight, sex, administration route, state of health, and severity of disease, the administration dose of the compound of the present invention is determined according to the instructions of a physician or pharmacist. Typically, the dose ranges from about 1 to 500 mg per day for an adult. For example, the compounds of the present invention may be intramuscularly or intravenously injected at a dose of from 5 to 300 mg per day to an adult. A higher dose may be effective for some patients.

A better understanding of the present invention may be obtained through the following examples which are set forth to illustrate, but are not to be construed as limiting the present invention.

Preparation Example 1

Preparation of Starting Material 1

The 4,6-dimethylpyrimidine compound, represented by Chemical Formula 2, serving as the starting material in Preparation Method 1 in accordance with the present invention, was prepared using a method well known in the organic chemistry field, as illustrated in the following Reaction Scheme 3. That is, the compound of Chemical Formula 7 was reacted with 2,4-pentadione in an aqueous potassium carbonate solution by heating under reflux.

[Reation scheme 3]

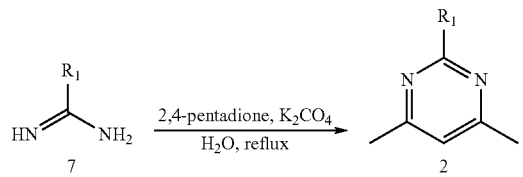

(wherein $R_1$ is as defined in Chemical Formula 1)

Preparation Example 2

Preparation of Starting Material 2

1,3-Bis(diethylphosphonomethyl)benzene, represented by Chemical Formula 5, serving as the starting material in Preparation Method 2 in accordance with the present invention, was prepared using the Arbuzof reaction well known in the organic chemistry field, as illustrated in the following Reaction Scheme 4. That is, α-dibromo-m-xylene was reacted with triethylphosphite in toluene by heating under reflux.

[Reaction Scheme 4]

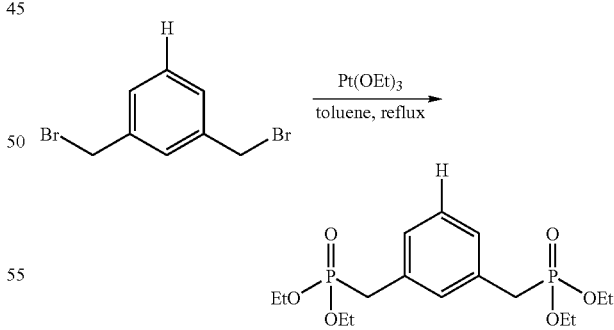

Preparation Example 3

Preparation of Starting Material 3

1,3-Bis(diethylphosphonomethyl)phenol, represented by Chemical Formula 5, serving as the starting material in Preparation Method 2 in accordance with the present invention, was prepared using the Arbuzof reaction well known in the organic chemistry field, as illustrated in the following Reaction Scheme 5. That is, 3,5-di(hydroxymethyl)phenol was dissolved in anhydrous 1,4-dioxane and reacted with BF$_3$.Et$_2$O and potassium iodide to give 3,5-bis(iodomethyl)phenol which was then heated together with triethylphosphite in toluene under reflux to afford 3,5-bis(diethylphosphonomethyl)phenol.

[Reaction Scheme 5]

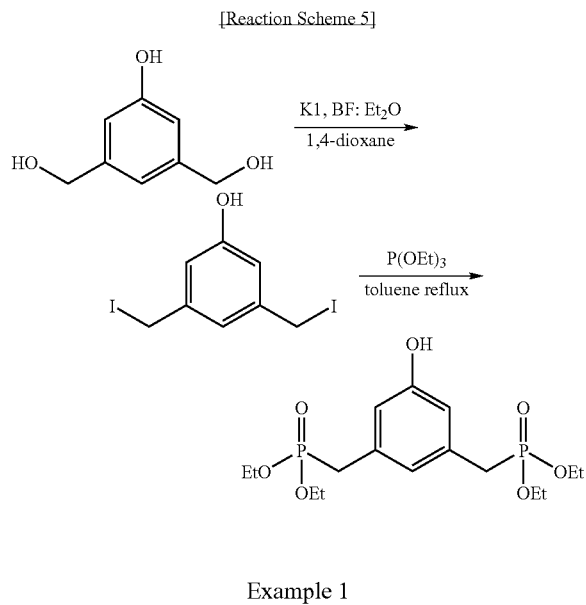

Example 1

Synthesis of (E,E)-4,6-Bis(3'-hydroxy-4'-methoxystyryl)pyrimidine

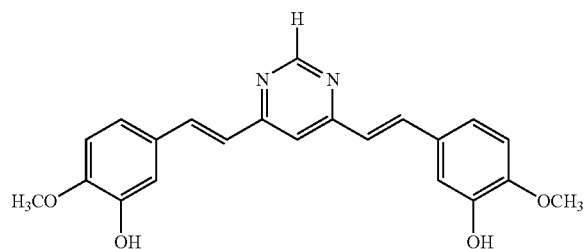 [SMILES: COc1ccc(/C=C/c2cc(/C=C/c3ccc(OC)c(O)c3)ncn2)cc1O]

Step 1: synthesis of (E,E)-4,6-bis[4'-methoxy-3'-(4''-methoxybenzyloxy)styryl]pyrimidine To 10 mL of an aqueous 5N sodium hydroxide solution were added 0.21 g (2.0 mmol) of 4,6-dimethylpyrimidine, 1.1 g (4 mmol) of 4-methoxy-3-(4-methoxybenzyloxy)benzaldehyde, and 0.1 g (0.29 mmol) of tetrabutylammonium hydrogen sulfate, followed by heating under reflux. The precipitate thus formed was filtered and washed with water. Then, it was dried in a vacuum drier and recrystallized in ethylacetate to afford 1.06 g of (E,E)-4,6-bis[4'-methoxy-3'-(4''-methoxybenzyloxy)styryl]pyrimidine.

$^1$H NMR (DMSOd$_6$, 400 MHz) δ 3.81 (s, 6H), 3.91 (s, 6H), 5.12 (s, 4H), 6.87 (d, J=15.9 Hz, 2H), 6.91 (d, J=8.6 Hz, 2H), 6.92 (d, J=8.5 Hz, 4H), 7.18 (d, J=8.6 Hz, 2H), 7.19 (s, 2H), 7.22 (s, 1H), 7.40 (d, J=8.5 Hz, 4H), 7.78 (d, J=15.9 Hz, 2H), 9.03 (s, 1H)

Step 2: synthesis of (E,E)-4,6-bis(3'-hydroxy-4'-methoxystyryl)pyrimidine 1.06 Grams of (E,E)-4,6-bis[4'-methoxy-3'-(4''-methoxybenzyloxy)styryl]pyrimidine, obtained in step 1, was dissolved in a mixture of 90 mL of ethanol and 30 mL of 1N HCl and heated under reflux for 20 hrs. The reaction mixture was cooled to room temperature and the precipitate thus formed was washed with water and hexane to afford 0.6 g of (E,E)-4,6-bis(3'-hydroxy-4'-methoxystyryl)pyrimidine (79%).

$^1$H NMR (DMSOd$_6$, 400 MHz) δ 3.80 (s, 6H), 6.97 (d, J=8.3 Hz, 2H), 6.98 (d, J=15.9 Hz, 2H), 7.11 (dd, J=1.9, 8.3 Hz, 2H), 7.13 (d, J=1.9 Hz, 2H), 7.62 (d, J=1.0 Hz, 1H), 7.78 (d, J=15.9 Hz, 2H), 8.95 (d, J=1.0 Hz, 1H), 9.17 (s, 2H)

Example 2

Synthesis of (E,E)-4,6-Bis[4'-hydroxy-3'-(N,N-dimethylamino)styryl]pyrimidine

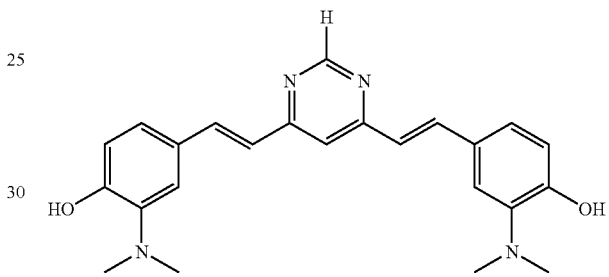

Step 1: Synthesis of (E,E)-4,6-bis[4'-(methoxymethoxy)-3'-(N,N-dimethylamino)styryl]pyrimidine To 10 mL of an aqueous 5N sodium hydroxide solution were added 0.21 g (2.0 mmol) of 4,6-dimethylpyrimidine, 0.83 g (4 mmol) of 3-(N,N-dimethylamino)-4-(methoxymethoxy)benzaldehyde, and 0.1 g (0.29 mmol) of tetrabutylammonium hydrogen sulfate, followed by heating under reflux for 5 hrs. The reaction mixture was extracted with ethylacetate and the organic layer thus formed was distilled in a vacuum. Purification through column chromatography gave 0.51 g of (E,E)-4,6-bis[4'-(methoxymethoxy)-3'-(N,N-dimethylamino)styryl]pyrimidine.

$^1$H NMR (DMSOd$_6$, 400 MHz) δ 2.77 (s, 12H), 3.42 (s, 6H), 5.24 (s, 4H), 7.05 (d, J=8.9 Hz, 2H), 7.11 (d, J=15.9 Hz, 2H), 7.23 (d, J=1.9 Hz, 2H), 7.24 (dd, J=1.9, 8.9 Hz, 2H), 7.67 (d, J=1.0 Hz, 1H), 7.87 (d, J=15.9 Hz, 2H), 8.97 (d, J=1.0 Hz, 1H)

Step 2: Synthesis of (E,E)-4,6-bis[4'-hydroxy-3'-(N,N-dimethylamino)styryl]pyrimidine 0.51 Grams of (E,E)-4,6-bis[4'-(methoxymethoxy)-3'-(N,N-dimethylamino)styryl]pyrimidine, obtained in step 1, was dissolved in a mixture of 45 mL of ethanol and 15 mL of 1N HCl and heated under reflux for 10 hrs. Then, the reaction mixture was cooled to room temperature and mixed with 1.26 g of sodium hydrogen carbonate. After the addition of 400 mL of water, the crystal thus formed was filtered to obtain 0.31 g of (E,E)-4,6-bis[4'-hydroxy-3'-(N,N-dimethylamino)styryl]pyrimidine (38%).

¹H NMR (DMSOd₆, 400 MHz) δ 2.73 (s, 12H), 6.81 (d, J=8.1 Hz, 2H), 7.01 (d, J=15.9 Hz, 2H), 7.16 (dd, J=1.8, 8.1 Hz, 2H), 7.19 (d, J=1.8 Hz, 2H), 7.59 (s, 1H), 7.81 (d, J=15.9 Hz, 2H), 8.93 (s, 1H), 9.62 (bs, 2H)

Example 3

Synthesis of (E,E)-1,3-Bis(3'-hydroxy-4'-methoxystyryl)benzene

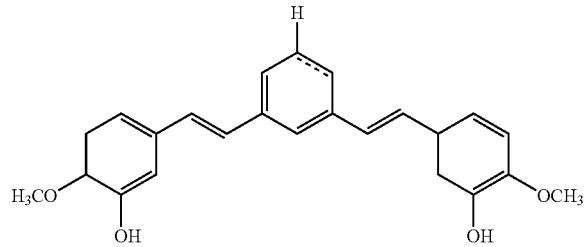

Step A: Synthesis of (E,E)-1,3-bis[4'-methoxy-3'-(methoxymethoxy)styryl]benzene

After being cooled to 0° C., a solution of 0.75 g of 1,3-bis(diethylphosphonomethyl)benzene and 0.78 g of 4-methoxy-3-(methoxymethoxy)benzaldehyde in THF was mixed with 0.88 g of potassium t-butoxide and allowed to stand for 2 hrs at room temperature. To the reaction mixture was added 200 mL of water and the precipitate thus formed was filtered to afford 0.69 g of (E,E)-1,3-bis[4'-methoxy-3'-(methoxymethoxy)styryl]benzene as a white solid.

¹H NMR (DMSOd₆, 400 MHz) δ 3.41 (s, 6H), 3.78 (s, 6H), 5.20 (s, 4H), 7.01 (d, J=8.5 Hz, 2H), 7.07 (d, J=16.4 Hz, 2H), 7.21 (dd, J=1.9, 8.5 Hz, 2H), 7.23 (d, J=16.4 Hz, 2H), 7.32-7.34 (m, 5H), 7.79 (s, 1H)

Step B: Synthesis of (E,E)-1,3-bis(3'-hydroxy-4'-methoxystyryl)benzene 0.69 Grams of (E,E)-1,3-bis[4'-methoxy-3'-(methoxymethoxy)styryl]benzene, obtained in step A, was dissolved in a mixture of 60 mL of ethanol and 20 mL of 1N HCl and heated under reflux for 1 hr. The reaction mixture was cooled to room temperature. After the addition of 100 mL of water to the reaction mixture, the precipitate thus formed was filtered to obtain 0.52 g of (E,E)-1,3-bis(3'-hydroxy-4'-methoxystyryl)benzene (77%).

¹H NMR (DMSOd₆, 400 MHz) δ 3.77 (s, 6H), 6.91 (d, J=8.3 Hz, 2H), 6.98 (d, J=16.3 Hz., 2H), 6.98 (dd, J=1.9, 8.3 Hz, 2H), 7.04 (d, J=1.9 Hz, 2H), 7.16 (d, J=16.3 Hz, 2H), 7.29-7.41 (m, 3H), 7.74 (s, 1H), 9.03 (s, 2H)

Various bis(styryl)pyrimidine derivatives were prepared in manners similar to those of Examples 1 and 2, and their structures and ¹H NMR data are summarized in Table 1, below.

TABLE 1

| Ex. No. | Structure | NMR Data |
|---|---|---|
| 4 | 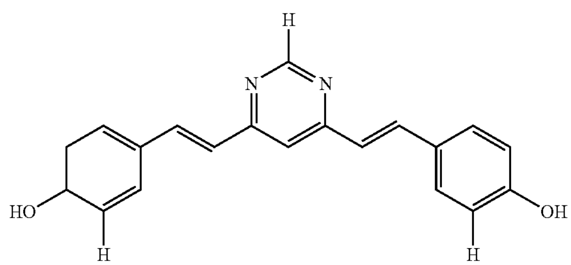 [SMILES: Oc1ccc(/C=C/c2cc(/C=C/C3=CCC(O)C=C3)ncn2)cc1] | 6.84 (d, J = 8.6 Hz, 4H), 7.06 (d, J = 16.0 Hz, 2H), 7.58 (d, J = 8.6 Hz, 4H), 7.67 (s, 1H), 7.90 (d, J = 16.0 Hz, 2H), 8.99 (s, 1H), 9.96 (bs, 2H) |
| 5 | 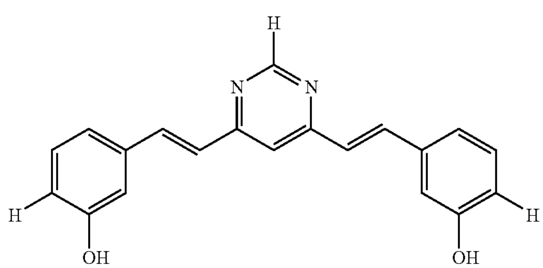 [SMILES: Oc1cccc(/C=C/c2cc(/C=C/c3cccc(O)c3)ncn2)c1] | 6.79 (dd, J = 1.7, 7.9 Hz, 2H), 7.07 (d, J = 1.7 Hz, 2H), 7.13-7.25 (m, 6H), 7.74 (d, J = 0.8 Hz, 1H), 7.84 (d, J = 16.0 Hz, 2H), 9.04 (d, J = 0.7 Hz, 1H), 9.57 (bs, 2H) |
| 6 | 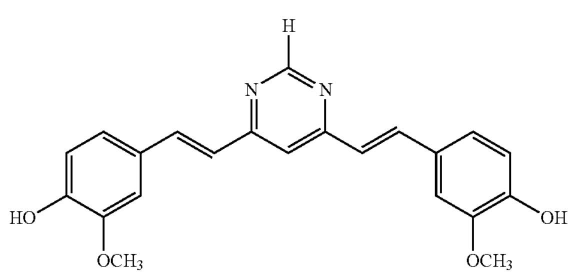 [SMILES: COc1cc(/C=C/c2cc(/C=C/c3ccc(O)c(OC)c3)ncn2)ccc1O] | 3.84 (s, 6H), 6.82 (d, J = 8.1 Hz, 2H), 7.09 (d, J = 16.0 Hz, 2H), 7.13 (dd, J = 1.6, 8.1 Hz, 2H), 7.32 (d, J = 1.6 Hz, 2H), 7.57 (s, 1H), 7.83 (d, J = 16.0 Hz, 2H), 8.95 (s, 1H), 9.48 (bs, 2H) |

TABLE 1-continued

| Ex. No. | Structure | NMR Data |
|---|---|---|
| 7 | 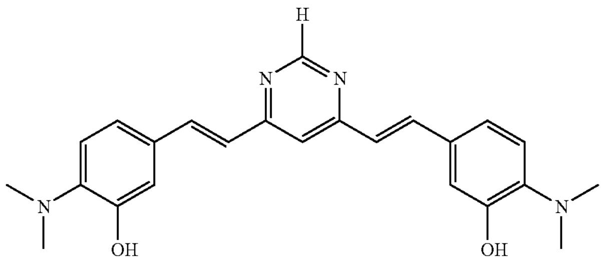 | 2.75 (s, 12H), 6.83 (d, J = 8.0 Hz, 2H), 6.91 (d, J = 15.9 Hz, 2H), 7.06 (d, J = 8.0 Hz, 2H), 7.07 (s, 2H), 7.63 (s, 1H), 7.76 (d, J = 15.9 Hz, 2H), 8.93 (s, 1H), 9.48 (bs, 2H) |
| 8 | 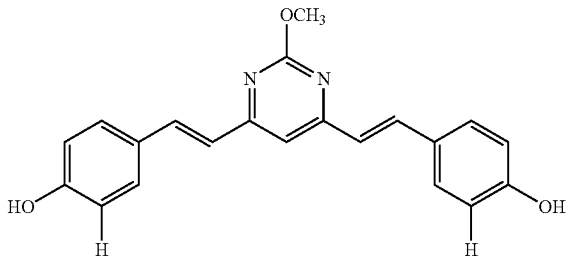 [SMILES: COc1nc(/C=C/c2ccc(O)cc2)cc(/C=C/c2ccc(O)cc2)n1] | .96 (s, 3H), 6.81 (d, J = 8.5 Hz, 4H), 6.98 (d, J = 15.9 Hz, 2H), 7.20 (s, 1H), 7.54 (d, J = 8.5 Hz, 4H), 7.79 (d, J = 15.9 Hz, 2H), 9.87 (bs, 2H) |
| 9 | 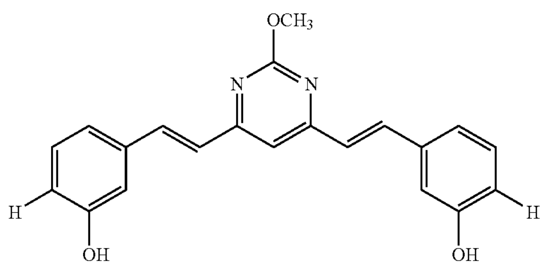 [SMILES: COc1nc(/C=C/c2cccc(O)c2)cc(/C=C/c2cccc(O)c2)n1] | 3.98 (s, 3H), 7.78 (dd, J = 1.8, 6.0 Hz, 2H), 7.05 (s, 2H), 7.11 (d, J = 15.9 Hz, 2H), 7.12 (d, J = 6.0 Hz, 2H), 7.22 (dd, J = 7.8, 7.8 Hz, 2H), 7.37 (s, 1H), 7.79 (d, J = 15.9 Hz, 2H), 9.58 (bs, 2H) |
| 10 | 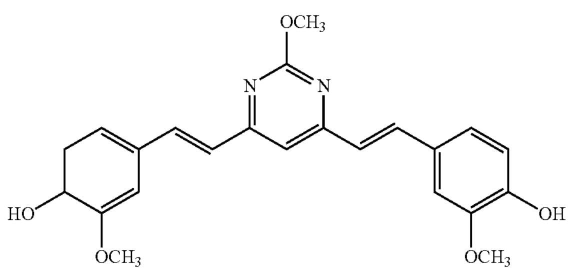 [SMILES: COC1=CC(/C=C/c2cc(/C=C/c3ccc(O)c(OC)c3)nc(OC)n2)=CCC1O] | 3.84 (s, 6H), 3.97 (s, 3H), 6.81 (d, J = 8.1 Hz, 2H), 7.04 (d, J = 15.9 Hz, 2H), 7.12 (dd, J = 1.7, 8.1 Hz, 2H), 7.22 (s, 1H), 7.30 (d, J = 1.7 Hz, 2H), 7.79 (d, J = 15.9 Hz, 2H), 9.53 (bs, 2H) |
| 11 | 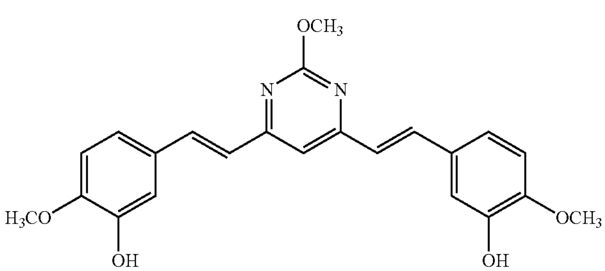 [SMILES: COc1nc(/C=C/c2ccc(OC)c(O)c2)cc(/C=C/c2ccc(OC)c(O)c2)n1] | 3.80 (s, 6H), 3.96 (s, 3H), 6.92-6.98 (m, 4H), 7.09-7.13 (m, 4H), 7.28 (s, 1H), 7.75 (d, J = 15.9 Hz, 2H), 9.18 (bs, 2H) |

TABLE 1-continued

| Ex. No. | Structure | NMR Data |
|---|---|---|
| 12 | 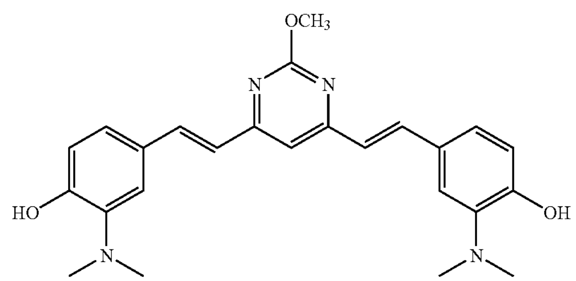 [SMILES: COc1nc(/C=C/c2ccc(O)c(N(C)C)c2)cc(/C=C/c2ccc(O)c(N(C)C)c2)n1] | 2.71 (s, 12H), 3.95 (s, 3H), 6.79 (d, J = 8.0 Hz, 2H), 6.94 (d, J = 15.9 Hz, 2H), 7.13 (dd, J = 1.8, 8.0 Hz, 2H), 7.17 (d, J = 1.8 Hz, 2H), 7.24 (s, 1H), 7.76 (d, J = 15.9 Hz, 2H), 9.58 (bs, 2H) |
| 13 | 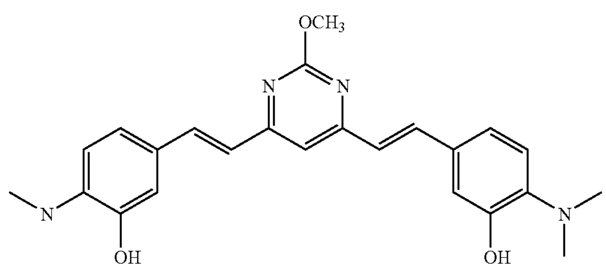 | 2.74 (s, 12H), 3.95 (s, 3H), 6.82 (d, J = 8.7 Hz, 2H), 6.85 (d, J = 15.8 Hz, 2H), 7.05-7.06 (m, 4H), 7.29 (s, 1H), 7.71 (d, J = 15.8 Hz, 2H), 9.36 (bs, 2H) |
| 14 | 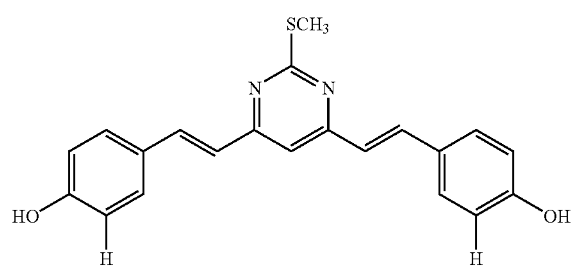 | 2.58 (s, 3H), 6.81 (d, J = 8.6 Hz, 4H), 6.96 (d, J = 15.9 Hz, 2H), 7.24 (s, 1H), 7.55 (d, J = 8.6 Hz, 4H), 7.79 (d, J = 15.9 Hz, 2H), 9.90 (bs, 2H) |
| 15 | 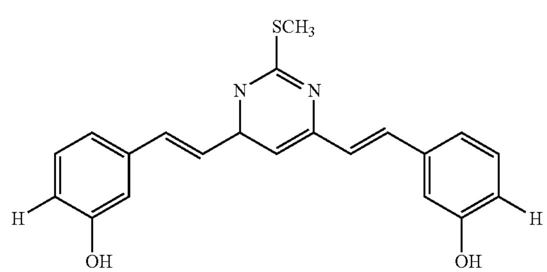 | 2.94 (s, 3H), 6.81 (d, J = 8.0 Hz, 2H), 7.09-7.27 (m, 8H), 7.81 (s, 1H), 7.89 (d, J = 15.9 Hz, 2H), 9.63 (bs, 2H) |
| 16 | 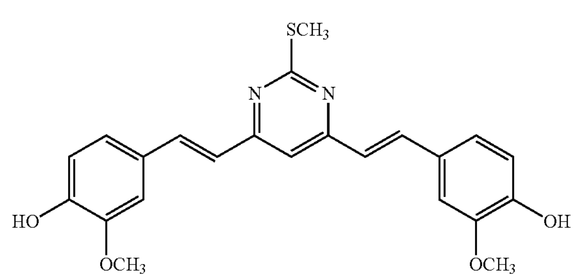 | 2.58 (s, 3H), 3.83 (s, 6H), 6.80 (d, J = 8.1 Hz, 2H), 7.02 (d, J = 15.9 Hz, 2H), 7.12 (dd, J = 1.6, 8.1 Hz, 2H), 7.25 (s, 1H), 7.30 (d, J = 1.6 Hz, 2H), 7.78 (d, J = 15.9 Hz, 2H), 9.47 (s, 2H) |

TABLE 1-continued

| Ex. No. | Structure | NMR Data |
|---|---|---|
| 17 | 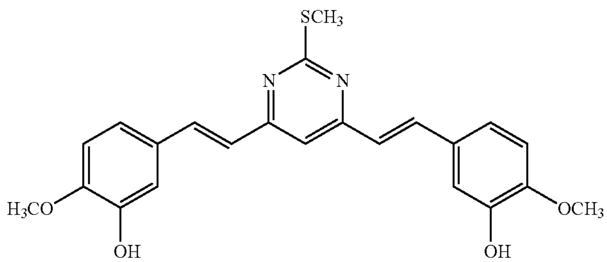 | 2.57 (s, 3H), 3.80 (s, 6H), 6.92 (d, J = 15.9 Hz, 2H), 6.96 (d, J = 8.3 Hz, 2H), 7.10 (dd, J = 1.9, 8.3 Hz, 2H), 7.13 (d, J = 1.9 Hz, 2H), 7.31 (s, 1H), 7.74 (d, J = 15.9 Hz, 2H), 9.17 (bs, 2H) |
| 18 | 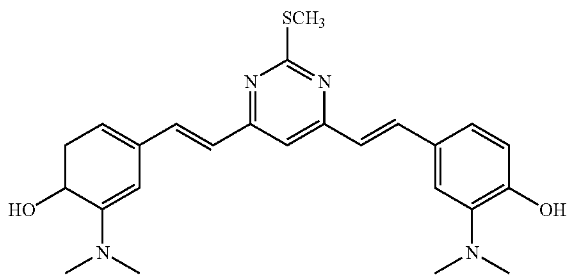 [SMILES: CSc1nc(/C=C/C2=CCC(O)C(N(C)C)=C2)cc(/C=C/c2ccc(O)c(N(C)C)c2)n1] | 2.57 (s, 3H), 2.71 (s, 12H), 6.79 (d, J = 8.1 Hz, 2H), 6.94 (d, J = 15.9 Hz, 2H), 7.15 (dd, J = 1.7, 8.1 Hz, 2H), 7.17 (d, J = 1.7 Hz, 2H), 7.29 (s, 1H), 7.76 (d, J = 15.9 Hz, 2H), 9.60 (bs, 2H) |
| 19 | 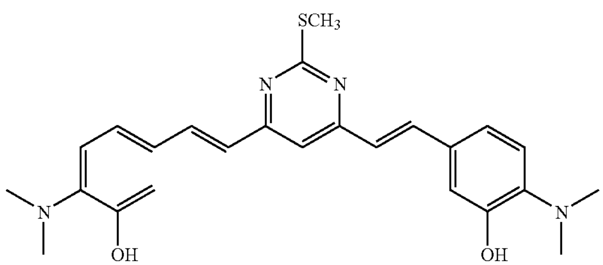 | 2.65 (s, 3H), 2.75 (s, 12H), 6.84-6.88 (m, 4H), 7.06-7.08 (m, 4H), 7.35 (s, 1H), 7.73 (d, 2H), 9.41 (bs, 2H) |

Procedures similar to that described in Example 3 were conducted to synthesize various bis(styryl)benzene compounds of which the structures and $^1$H NMR data are summarized in Table 2, below.

TABLE 2

| Ex. No. | Structure | NMR Data |
|---|---|---|
| 20 | 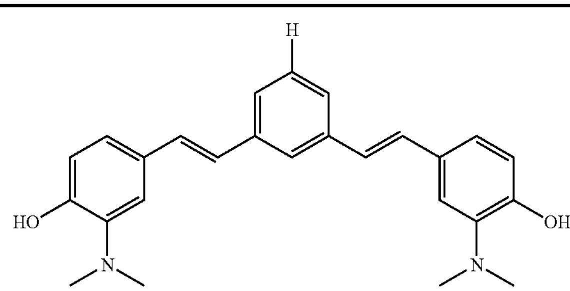 | 2.71 (s, 12H), 6.75 (d, J = 8.1 Hz, 2H), 7.00 (d, J = 15.6 Hz, 2H), 7.03 (d, J = 8.1 Hz, 2H), 7.10 (s, 2H), 7.18 (d, J = 15.6 Hz, 2H), 7.27-7.37 (m, 3H), 7.74 (s, 1H), 9.25 (bs, 2H) |
| 21 | 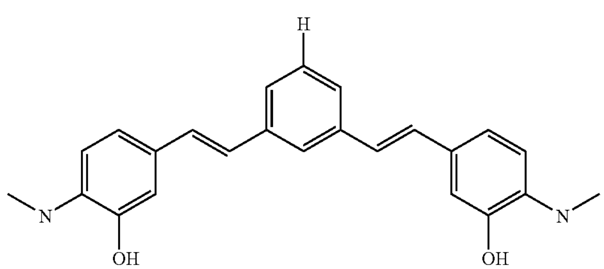 | 2.69 (s, 12H), 6.82 (d, J = 8.1 Hz, 2H), 6.94 (d, J = 16.3 Hz, 2H), 6.96 (dd, J = 1.7, 8.1 Hz, 2H), 6.99 (d, J = 1.7 Hz, 2H), 7.15 (d, J = 16.3 Hz, 2H), 7.28-7.39 (m, 3H), 7.73 (s, 1H), 9.11 (s, 2H) |

TABLE 2-continued

| Ex. No. | Structure | NMR Data |
|---|---|---|
| 22 | 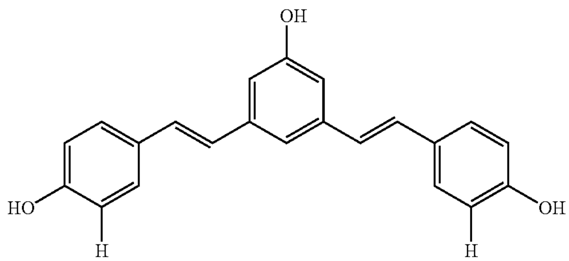 [SMILES: Oc1ccc(/C=C/c2cc(O)cc(/C=C/c3ccc(O)cc3)c2)cc1] | 6.75 (d, J = 8.5 Hz, 4H), 6.78 (s, 2H), 6.91 (d, J = 16.3 Hz, 2H), 7.07 (d, J = 16.3 Hz, 2H), 7.16 (s, 1H), 7.41 (d, J = 8.5 Hz, 4H), 9.38 (bs, 1H), 9.56 (bs, 2H) |
| 23 | 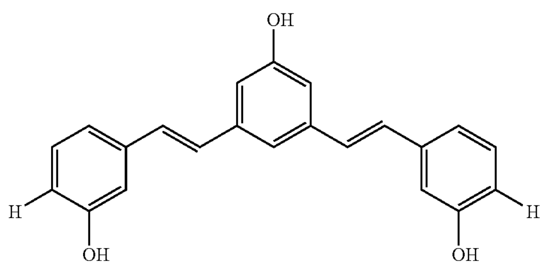 [SMILES: Oc1cccc(/C=C/c2cc(O)cc(/C=C/c3cccc(O)c3)c2)c1] | 6.65-6.68 (m, 2H), 6.86 (s, 2H), 6.95 (s, 2H), 7.02 (d, J = 7.8 Hz, 2H), 7.05 (d, J = 16.2 Hz, 2H), 7.12 (d, J = 16.2 Hz, 2H), 7.15 (dd, J = 7.8, 7.8 Hz, 2H), 7.28 (s, 1H), 9.42 (s, 2H), 9.48 (s, 1H) |
| 24 | 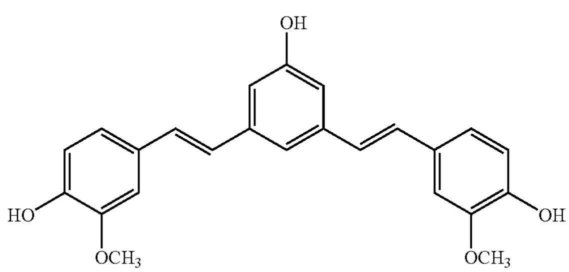 | 3.81 (s, 6H), 6.75 (d, J = 8.1 Hz, 2H), 6.78 (s, 2H), 6.97 (d, J = 16.3 Hz, 2H), 6.97 (dd, J = 1.5, 8.1 Hz, 2H), 7.08 (d, J = 16.3 Hz, 2H), 7.18 (d, J = 1.5 Hz, 2H), 7.19 (s, 1H), 9.13 (bs, 2H), 9.39 (s, 1H) |
| 25 | 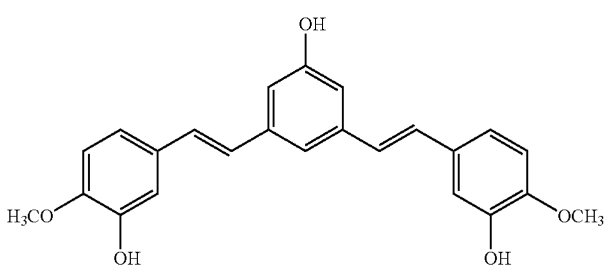 [SMILES: COc1ccc(/C=C/c2cc(O)cc(/C=C/c3ccc(OC)c(O)c3)c2)cc1O] | 3.77 (s, 6H), 6.79 (d, J = 1.0 Hz, 2H), 6.99 (d, J = 16.4 Hz, 2H), 6.90 (d, J = 8.3 Hz, 2H), 6.97 (dd, J = 1.9, 8.3 Hz, 2H), 7.02 (d, J = 1.9 Hz, 2H), 7.05 (d, J = 16.4 Hz, 2H), 7.20 (s, 1H), 9.00 (bs, 2H), 9.40 (bs, 1H) |
| 26 | 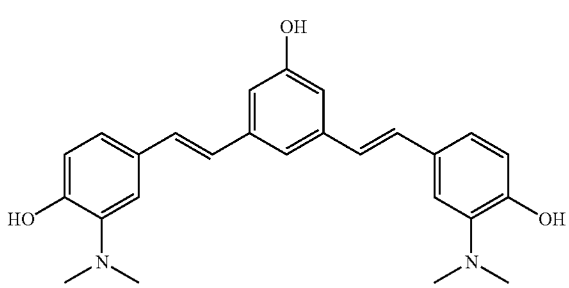 [SMILES: CN(C)c1cc(/C=C/c2cc(O)cc(/C=C/c3ccc(O)c(N(C)C)c3)c2)ccc1O] | 2.69 (s, 12H), 6.74 (d, J = 8.0 Hz, 2H), 6.76 (s, 2H), 6.90 (d, J = 16.3 Hz, 2H), 7.01 (dd, J = 1.7, 8.0 Hz, 2H), 7.06 (d, J = 16.3 Hz, 2H), 7.08 (d, J = 1.7 Hz, 2H), 7.20 (s, 1H), 9.24 (bs, 2H), 9.36 (bs, 1H) |

TABLE 2-continued

| Ex. No. | Structure | NMR Data |
|---|---|---|
| 27 | 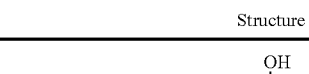 | 2.77 (s, 12H), 6.82 (s, 2H), 6.90 (d, J = 16.3 Hz, 2H), 7.00-7.02 (m, 6H), 7.07 (d, J = 16.3 Hz, 2H), 7.23 (s, 1H), 9.34 (s, 2H), 9.43 (bs, 1H) |

Test Example 1

Assay for Inhibitory Activity Against Beta Amyloid Fibril Formation

The compounds of the present invention were assayed for inhibitory activity against the formation of beta amyloid fibrils as a function of ThT fluorescence intensity as follows.

Beta amyloid (1-42) and each of the compounds of Examples 1 to 27 were dissolved in DMSO and diluted with PBS (phosphate-buffered saline, pH 7.4). The final concentrations of beta amyloid (1-42) (control) and each of the compounds of Examples 1 to 27 were set at 25 μM and 10 μM, respectively. The dilutions were incubated at room temperature for 1 hr before a solution of thioflavin T (ThT, 5 μM, pH 8.5) in glycin-NaOH buffer was added thereto. Fluorescence was measured at 450 nm for excitation (slit 10 nm) and 458 nm for emission (slit 10 nm) on 96-well microplates using a multilabel fluorescence counter. The results are summarized in Table 3, below.

TABLE 3

| Cpd. | Fibril Formation (%) |
|---|---|
| Control | 100 ± 10.7 |
| Ex. 1 | 19.1 ± 0.6 |
| Ex. 2 | 16.5 ± 2.6 |
| Ex. 3 | 32.1 ± 1.1 |
| Ex. 4 | 35.7 ± 7.0 |
| Ex. 5 | 85.9 ± 19.7 |
| Ex. 6 | 20.7 ± 5.4 |
| Ex. 7 | 6.3 ± 1.8 |
| Ex. 8 | 32.6 ± 7.3 |
| Ex. 9 | 128.7 ± 11.6 |
| Ex. 10 | 32.0 ± 11.6 |
| Ex. 11 | 45.0 ± 9.2 |
| Ex. 12 | 25.9 ± 7.3 |
| Ex. 13 | 9.6 ± 3.7 |
| Ex. 14 | 32.6 ± 7.4 |
| Ex. 15 | 153.3 ± 16.3 |
| Ex. 16 | 32.4 ± 12.5 |
| Ex. 17 | 24.8 ± 11.1 |
| Ex. 18 | 21.4 ± 10.3 |
| Ex. 19 | 11.2 ± 4.2 |
| Ex. 20 | 36.1 ± 10.1 |
| Ex. 21 | 44 ± 8.3 |
| Ex. 22 | 19.3 ± 1.1 |
| Ex. 23 | 92.9 ± 12.4 |
| Ex. 24 | 21 ± 2.4 |
| Ex. 25 | 15.5 ± 3.8 |
| Ex. 26 | 25.8 ± 5.8 |
| Ex. 27 | 16.7 ± 0.7 |

With reference to Table 3, lower ThT fluorescence intensities, indicative of lower levels of beta amyloid fibrils, were detected when beta amyloid (1-42) was incubated in combination with the compounds of the Examples than when alone (control), demonstrating that the compounds of the Examples in accordance with the present invention are inhibitory of the formation of beta amyloid fibrils. Particularly, the compounds of Examples 7 and 13 were found to have remarkable inhibitory activity against fibril formation.

Test Example 2

Assay for Cytotoxicity in HT-22 Cell

The following experiment was performed with HT-22 cells in order to examine the cytotoxicity of the compounds of the Examples in accordance with the present invention.

The murine hippocampal neuronal cell line HT-22 was incubated at 37° C. in DMEM (Dulbecco's Modified Eagle's Medium) supplemented with 10% FBS (fetal bovine serum) and 1% penicillin/streptomycin in a 5% $CO_2$ incubator. Before testing, HT-22 cells were seeded at a density of $5 \times 10^3$ cells/well onto 96-well plates containing serum-free DMEM and incubated for 1 hr. Afterwards, each of the compounds of Examples 1 to 27 was added at a concentration of 25 μM to each well before incubation for 18 hrs. 5 mg/ml MTT (3-(4, 5-dimethyl-2-thiozolyl)-2,5-diphenyl-2H-tetrazolium bromide) solution was added in an amount of 15 μl per well and incubated for 4 hrs. A solubilization solution (10% SDS, 50% dimethylformamide, pH 4.7) was added in an amount of 100 μl to each well, followed by incubation for 18 hrs. Absorbance at 570 nm/630 nm was read on a microplate reader. The results are summarized in Table 4, below.

TABLE 4

| Cpd. | Cell Survival (%) |
|---|---|
| Ex. 1 | 135.6 ± 6.1 |
| Ex. 2 | 146.2 ± 26.6 |
| Ex. 3 | 69.5 ± 4.2 |
| Ex. 4 | 104.2 ± 7.1 |
| Ex. 5 | 142.5 ± 5.6 |
| Ex. 6 | 215.6 ± 3.5 |
| Ex. 7 | 132.8 ± 41.1 |
| Ex. 8 | 101.2 ± 31.8 |
| Ex. 9 | 45.9 ± 4.2 |
| Ex. 10 | 75.2 ± 12.5 |
| Ex. 11 | 98.4 ± 2.7 |
| Ex. 12 | 96.6 ± 13.7 |
| Ex. 13 | 101.4 ± 2.5 |
| Ex. 14 | 65.3 ± 6.0 |
| Ex. 15 | 43.7 ± 6.6 |
| Ex. 16 | 79.0 ± 7.9 |
| Ex. 17 | 78.8 ± 9.3 |
| Ex. 18 | 77.3 ± 15.1 |

TABLE 4-continued

| Cpd. | Cell Survival (%) |
|---|---|
| Ex. 19 | 85.3 ± 8.1 |
| Ex. 20 | 95.7 ± 8.3 |
| Ex. 21 | 100.8 ± 7.6 |
| Ex. 22 | 37.4 ± 4.7 |
| Ex. 23 | 59.2 ± 15.4 |
| Ex. 24 | 80.9 ± 13.1 |
| Ex. 25 | 73.5 ± 14.1 |
| Ex. 26 | 66.0 ± 12.1 |
| Ex. 27 | 64.4 ± 4.2 |

With reference to Table 4, almost all of the compounds of the Examples in accordance with the present invention ensure 70% or higher survival rates of HT-22 cells. Therefore, it is apparent from the data of Table 4 that the compounds according to the present invention are not toxic to cells.

Test Example 3

Alleviating Effect of Compounds on Beta Amyloid (1-42) Toxicity

The following experiment was performed in order to examine the ability of the compounds of the Examples in accordance with the present invention to alleviate beta amyloid toxicity. HT-22 cells were cultured and incubated with the compounds of Examples 1 to 27 for 1 hr in the same manner as in Example 2. Cell necrosis was induced by beta amyloid toxicity. For this, the cells were incubated with 25 μM of beta amyloid (Aβ25-35) for 18 hrs. Subsequently, a 5 mg/ml MTT solution was added in an amount of 15 μl to each well, followed by incubation for 4 hrs. Then, the cells were again incubated for 18 hrs with 100 μl/well of the solubilization solution. Absorbance at 570 nm/630 nm was read on a microplate reader. The results are summarized in Table 5, below.

TABLE 5

| Cpd. | Cell Survival (%) |
|---|---|
| Aβ25-35 | 56.0 ± 0.6 |
| Ex. 1 | 91.8 ± 8.8 |
| Ex. 2 | 85.3 ± 0.1 |
| Ex. 3 | 54.7 ± 5.3 |
| Ex. 4 | 81.0 ± 1.2 |
| Ex. 5 | 43.5 ± 13.4 |
| Ex. 6 | 103.0 ± 13.0 |
| Ex. 7 | 76.6 ± 12.1 |
| Ex. 8 | 100.5 ± 7.0 |
| Ex. 9 | 47.7 ± 3.3 |
| Ex. 10 | 71.7 ± 14.8 |
| Ex. 11 | 66.2 ± 11.5 |
| Ex. 12 | 59.0 ± 5.7 |
| Ex. 13 | 67.4 ± 5.1 |
| Ex. 14 | 34.2 ± 4.0 |
| Ex. 15 | 39.6 ± 0.4 |
| Ex. 16 | 49.0 ± 4.2 |
| Ex. 17 | 78.3 ± 0.4 |
| Ex. 18 | 50.9 ± 5.7 |
| Ex. 19 | 69.7 ± 0.4 |
| Ex. 20 | 45.8 ± 9.1 |
| Ex. 21 | 52.8 ± 7.2 |
| Ex. 22 | 50.6 ± 10.1 |
| Ex. 23 | 47.7 ± 11.1 |
| Ex. 24 | 39.9 ± 9.5 |
| Ex. 25 | 43.2 ± 10.0 |
| Ex. 26 | 47.4 ± 0.6 |
| Ex. 27 | 50.5 ± 3.9 |

As is apparent from the data of Table 5, the compounds of the Examples in accordance with the present invention significantly alleviated the cytotoxicity of beta amyloid (Aβ25-35), thus increasing cell survival.

Test Example 4

Induction of Acute Alzheimer's Disease by Administration of Beta Amyloid and Improvement in Learning and Memory by Administration of Compounds The compounds of the Examples in accordance with the present invention were assayed for ability to recover learning and memory in mice administered with beta amyloid.

Step 1: Administration of beta amyloid (1-42) and Compounds to Mice

Mice 4-5 weeks old, each weighing 20~25 g, were divided into groups of six. Intracerebroventricular injection was performed with a 50 μl Hamilton microsyringe fitted with a disposable 26-gauge needle as described by Laursen and Belknap (Laursen & Belknap, J. Pharmacol. Methods. 1986, 16, 355). It was inserted 2.4 mm deep into the bregma. All samples were administered to groups of 10 via oral routes or food pellets. After the intracerebroventricular injection, the compounds of the present invention were administered for 2 days to the mice which were then subjected to the Y-maze test on Day 2, the cognition test on Days 2 and 3, the passive avoidance test on Days 3 and 4, and the water maze test on Days 3 to 7. All data were averages of 6 measurements (mice).

Step 2: Animal Tests with Acute Alzheimer's Disease (AD) Model—Y-Maze, Cognition, Passive Avoidance and Water Maze Short-term memory was assessed by spontaneous alternation behavior in the Y-maze task. Spontaneous alternation behavior is considered to reflect spatial working memory, which is a form of short-term memory. A mouse was placed in one arm of a Y-maze and allowed to freely pass the three arms for 8 min. Spontaneous alternation behavior was defined as successive entries into the three arms. Percentage spontaneous alternation was calculated as the ratio of actual to possible alternations (defined as the total number of arm entries), multiplied by 100.

For the cognitive performance task, two identical substances were respectively placed 5 cm apart from two corners and the time it took for a mouse to investigate the given and new substances was measured. Investigation was defined as the condition in which a mouse sniffed with the head directing toward the substance within a diameter of 2 cm or touched the substance.

A passive avoidance test was performed as described in the literature (Song et al. J. Neurochem., 1998, 71, 875). Used was a passive avoidance box which was divided into two compartments: a lighted one and a dark one, separated by an automatic guillotine door. For training, mice were placed in the lighted compartment and electrically shocked with 0.25 mA for 1 sec whenever they entered the darkened compartment. 24 hours after training, the mice were placed in the lighted compartment and measured for latency time before entering the darkened compartment.

In a water maze test, a mouse, when released from a randomly selected quadrant on each trial, was allowed to swim around the pool in search of an exit while the time taken to reach the platform (latency) was recorded. When the mouse did not locate the platform within 60 sec, it was guided to the platform.

The results are shown in Table 6 and FIGS. 1 and 2.

TABLE 6

| | Behavior Tests | | | | |
|---|---|---|---|---|---|
| | Y-Maze Spontaneous | Cognition | | Passive Avoidance | |
| Cpd | Alternation (%)$^a$ | Preference$^b$ | % of control | Latency (sec) | % of control |
| Control | — | 0.64 ± 0.02 | — | 178.1 | 100 |
| Aβ1-42 | 61.6 | 0.54 ± 0.02 | 84 | 89.9 | 50.4 |
| Ex. 1 | 72.2 | 0.59 ± 0.03 | 92 | 144.2 | 80.9 |
| Ex. 2 | 71.3 | 0.53 ± 0.05 | 82 | 117.8 | 66.1 |
| Ex. 6 | 67.9 | 0.61 ± 0.03 | 95 | 139.2 | 78.1 |
| Ex. 7 | 67.0 | 0.57 ± 0.02 | 89 | 122.5 | 68.7 |

$^a$% spontaneous alternation = (actual/possible alternations) × 100
$^b$Cognitive Preference = investigation time for new matter/total investigation time As understood from the data of Table 6, the beta amyloid (1-42) injected mice had with statistical significance increased memory following administration with the compounds of Examples 1, 2, 6 and 7, as compared to those before the administration. The beta amyloid (1-42) injected mice had a reduced preference for the new matter by about 16% compared to the control, but recovered memory by as high as about 11% when administered with the compound of Example 6. In the passive avoidance test, the beta amyloid (1-42) injected mice showed only about 50% of the cognitive performance of the control, but it was improved by about 16-30% in the mice that were administered with the compounds of the Examples, with the highest improvement being shown for the compound of Example 1.

With reference to FIG. 1, results of the water maze task designed to test spatial learning abilities of mice are depicted in graphs. As seen in these graphs, the mice injected with beta amyloid (1-42) alone were deficient in spatial memory whereas when additionally administered with the compounds of Examples 1 and 6 (A) and 2 and 7 (B), the mice were observed to recover spatial learning ability with the lapse of time as the latency was shortened with an increasing number of the sessions.

With reference to FIG. 2, the compound of Example 1 shows learning and memory improvement effects in a dose-dependent manner.

Taken together, the data obtained above demonstrate that the four compounds according to the present invention enhance memory and learning ability, thus being useful in the prevention and treatment of amyloidosis-associated diseases.

Test Example 5

Effect on Learning and Memory of Transgenic Mice

The effects of the compounds of the Examples according to the present invention on the learning and memory of transgenic mice were examined through the following tests.

Double transgenic mice with mutations in both APP and presenilin 1 were used for the tests. The double transgenic mice, each weighing 26-39 g, were eight months old. They were divided into groups of 10 and administered for 2 to 3 months with the compound of Example 1 through food pellets (3 mg/pellet) before conducting the behavior tests.

After administration of the compound of Example 1 for 2 months (for 10 month old mice), the mice were tested for learning and memory through the Y-maze task and cognitive performance tests. The results are graphically shown in FIGS. 3A and 3B.

As seen in FIGS. 3A and 3B, the beneficial effect of the compounds of the present invention on learning and memory ability, although slightly lower than in the acute AD model, was significant in the transgenic mice, such that the memory impairment was alleviated in the transgenic mice administered with the compound of Example 1.

A memory test was performed in context fear conditioning. Five trials of tone-shock pairing of CS-US (conditioned stimulus-unconditioned stimulus) were given to mice. On the next day, the mice were left in the stimulated context under no stimulus conditions and observed for freezing. The results are graphically shown in FIG. 3C. As seen in the graph of FIG. 3C, the mice treated with the compound of Example 1 spent a longer time freezing than did the control, suggesting that the hippocampal damage caused by the beta amyloid aggregates was alleviated. During the test, there was no difference in average body weight between the two groups.

The compound of Example 1 was found to improve learning and memory abilities as demonstrated by the behavior assay. In order to examine whether this effect resulted from inhibitory activity against the deposition of beta amyloid or from a decrease in the level of beta amyloid, the cerebra of the transgenic mice were immunohistochemically analyzed. In this regard, after being removed from the transgenic mice which were 11 months old upon completion of the behavior test, the right cerebral hemispheres were measured for amyloid plaque levels in the cerebral cortex and hippocampus using an immunostaining or ELISA (Enzyme-linked immunosorbent assay) method. The results are given in FIG. 4.

Figure 4B:
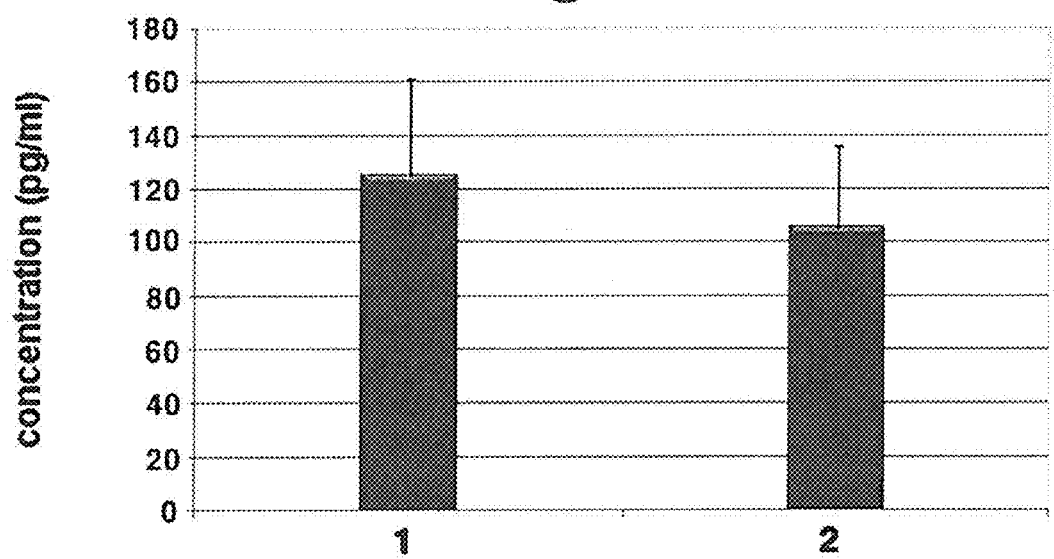
FIG. 4 shows results of the immmunohistochemical analysis of the cerebra from the transgenic mice of Test Example 5 designed to examine whether the improvement in learning and memory by the compound of the present invention results from inhibitory activity against the deposition of beta amyloid or from a decrease in beta amyloid levels ((A): counts of amyloid plaques stained with Congo Red; (B): ELISA assay for beta amyloid (1-40); (C): ELISA assay for beta amyloid (1-42); (D): counts of neurons).

Amyloid plaques were stained with Congo red and counted. As seen in FIG. 4A, counts of the amyloid plaques were smaller in the group treated with the compound of Example 1 than in the control. The levels of beta amyloids (1-40) and (1-42) were determined using ELISA and are given in FIGS. 4B and 4C, respectively, showing a decreasing pattern similar to that of amyloid plaques. FIG. 4D gives neuronal cell count data, showing a larger crowd in the group treated with the compound of Example 1.

Taken together, the data obtained above demonstrate that the derivatives of Chemical Formula 1 in accordance with the present invention inhibit the cerebral deposition of beta amyloid, thereby alleviating the toxicity of beta amyloid and protecting neurons from the toxicity. Therefore, the compounds of the present invention can be useful in the prevention and treatment of amyloidosis-associated diseases.

Having the ability to inhibit the deposition of beta amyloid and to reduce the toxicity of beta amyloid, as described hitherto, the derivatives of Chemical Formula 1 in accordance with the present invention can improve learning and memory and can be useful in the prevention and treatment of neurodegenerative diseases such as Alzheimer's disease and the like.

It is exemplified a Formulation for an agent of prevention and treatment of neurodegenerative diseases according to the present invention, below.

Formulation Example 1

Pharmaceutical Formulations 1-1. Preparation of Powder

| | |
|---|---|
| The bis(styryl)pyridine or bis(styryl)benzene compound of the Chemical Formula 1 | 2 g |
| Lactose | 1 g |

Powder product was prepared by mixing the above ingredients and filling an airtight package therewith.

1-2. Preparation of Tablet

| | |
|---|---|
| The bis(styryl)pyridine or bis(styryl)benzene compound of the Chemical Formula 1 | 100 mg |
| Corn starch | 100 mg |
| Lactose | 100 mg |
| Magnesium stearate | 2 mg |

Tablets were prepared by mixing the above ingredients and tabletting by a conventional method.

1-3. Preparation of Capsule

| | |
|---|---|
| The bis(styryl)pyridine or bis(styryl)benzene compound of the Chemical Formula 1 | 100 mg |
| Corn starch | 100 mg |
| Lactose | 100 mg |
| Magnesium stearate | 2 mg |

Capsules were prepared by mixing the above ingredients and filling a gelatin capsule by a conventional method.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A compound of bis(styryl)pyrimidine, represented by the following Chemical Formula 1, or pharmaceutically acceptable salts thereof:

(Chemical Formula 1)

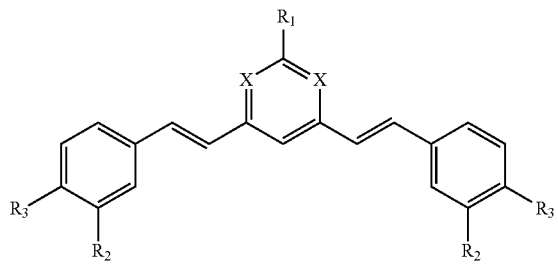

Wherein
x is nitrogen;
$R_1$ is selected from the group consisting of methoxy, ethoxy, propyloxy, butyloxy; and
$R_2$ and $R_3$ are independently selected from hydrogen, hydroxy, methoxy, ethoxy, propoxy, butoxy, dimethylamino, diethylamino, dipropylamino, and dibutylamino.

2. The compound of bis(styryl)pyrimidine or pharmaceutically acceptable salts thereof of claim 1, wherein
X is nitrogen;
$R_1$ is selected from the group consisting of methoxy and ethoxy; and
$R_2$ and $R_3$ are independently selected from the group consisting of hydrogen, hydroxy, methoxy, ethoxy, dimethylamino and diethylamino.

3. The compound of bis(styryl)pyrimidine or pharmaceutically acceptable salts thereof of claim 1, selected from the group consisting of:
(1) 2-methoxy-(E,E)-4,6-bis(4'-hydroxystyryl)pyrimidine;
(2) 2-methoxy-(E,E)-4,6-bis(3'-hydroxystyryl)pyrimidine;
(3) 2-methoxy-(E,E)-4,6-bis(4'-hydroxy-3'-methoxystyryl)pyrimidine;
(4) 2-methoxy-(E,E)-4,6-bis(3'-hydroxy-4'-methoxystyryl)pyrimidine;
(5) 2-methoxy-(E,E)-4,6-bis[4'-hydroxy-3'-(N,N-dimethylamino)styryl]pyrimidine;
(6) 2-methoxy-(E,E)-4,6-bis[3'-hydroxy-4'-(N,N-dimethylamino)styryl]pyrimidine.

4. A method for preparing the compound of bis(styryl)pyrimidine of claim 1, described as Chemical Formula 1a in the following Reaction Scheme 1, comprising:
(1) preparing a compound of Chemical Formula 4 by condensating a pyrimidine compound of Chemical Formula 2 with a benzaldehyde compound of Chemical Formula 3 in an alkaline condition (Step 1); and
(2) deprotecting the compound of Chemical Formula 4 (Step 2), as described in the following Reaction Scheme 1:

(Reaction Scheme 1)

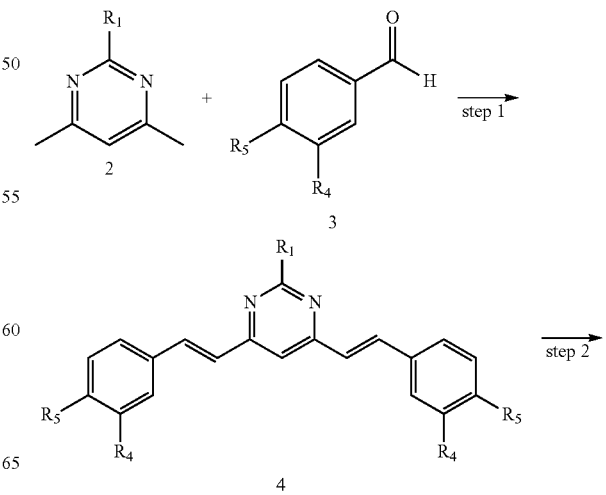

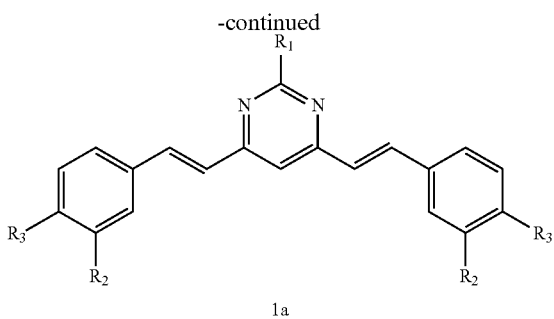

1a (wherein, $R_1$, $R_2$ and $R_3$ are as defined in the Chemical Formula 1 of claim 1; $R_4$ and $R_5$ are respectively the same as $R_2$ and $R_3$, provided that they are independently p-methoxybenzyl or methoxymethyl when $R_2$ and $R_3$ are independently hydroxyl.

5. The method of claim 4, wherein the condensating in Step 1 is performed by refluxing a solution of the compound of Chemical Formula 2 and the compound of Chemical Formula 3 in the presence of a phase transfer catalyst (PTC) in an alkaline solution.

6. The method of claim 5, wherein the phase transfer catalyst is tetrabutylammonium hydrogen sulphate ($Bu_4NHSO_4$) or benzyltrimethylammonium.

7. The method of claim 5, wherein the deprotecting of step (2) is performed by refluxing in a HCl/ethanol (3:1) solvent or by stirring in a methylene chloride solvent in the presence of trifluoroacetic acid.

8. A method for treating diseases associated with beta-amyloid deposition, comprising administering the compound of the Chemical Formula 1 or pharmaceutically acceptable salts thereof of claim 1 in a therapeutically effective amount to a subject in need thereof, wherein the disease associated with beta-amyloid deposition is Alzheimer's disease.

9. The method for treating Alzheimer's disease of claim 8, wherein the compound of the Chemical Formula 1 or pharmaceutically acceptable salts thereof of claim 1 inhibit the deposition of beta amyloid.

10. A method for treating Alzheimer's disease, comprising administering of a compound of bis(styryl)pyrimidine of the Chemical Formula 1 or pharmaceutically acceptable salts thereof at a dose of from about 0.1 to 1,500 mg a day for an adult:

(Chemical Formula 1)

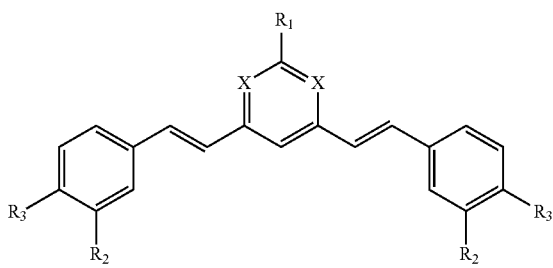

Wherein
x is nitrogen;
$R_1$ is selected from the group consisting of methoxy, ethoxy, propyloxy, and butyloxy; and
$R_2$ and $R_3$ are independently selected from hydrogen, hydroxy, methoxy, ethoxy, propoxy, butoxy, dimethylamino, diethylamino, dipropylamino, and dibutylamino.

11. The compound of bis(styryl)pyrimidine or pharmaceutically acceptable salts thereof of claim 10, wherein the propoxy of the $R_1$ is selected from the group consisting of isopropoxy and n-propoxy.

12. The compound of claim 10, wherein the butoxy of the $R_1$ is selected from the group consisting of n-butoxy, sec-butoxy, isobutoxy, and tert-butoxy.

13. The compound of bis(styryl)pyrimidine or pharmaceutically acceptable salts thereof of claim 1, wherein the $R_2$ is selected from the group consisting of methoxy, ethoxy, isopropoxy, n-propoxy, n-butoxy, sec-butoxy, isobutoxy, tert-butoxy, dimethylamino, diethylamino, di-isopropylamino, di-n-propylamino, di-n-butylamino, di-sec-butylamino, di-isobutylamino, and di-tert-butylamino.

14. The compound of bis(styryl)pyrimidine or pharmaceutically acceptable salts thereof of claim 1, wherein the $R_3$ is selected from the group consisting of methoxy, ethoxy, isopropoxy, n-propoxy, n-butoxy, sec-butoxy, isobutoxy, tert-butoxy, dimethylamino, diethylamino, di-isopropylamino, di-n-propylamino, and di-n-butylamino, di-sec-butylamino, di-isobutylamino, and di-tert-butylamino.

15. A method for treating Alzheimer's disease, comprising administering of a capsule comprising 100 mg corn starch, 100 mg lactose, 2 mg magnesium stearate, and 100 mg of a compound of bis(styryl)pyrimidine of the Chemical Formula 1 or pharmaceutically acceptable salts thereof:

(Chemical Formula 1)

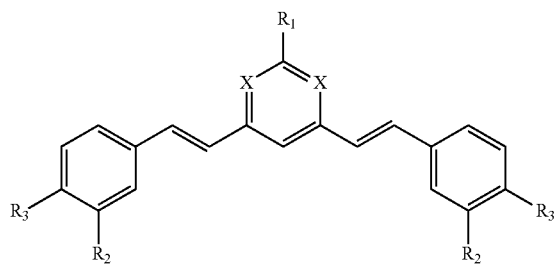

Wherein
x is nitrogen;
$R_1$ is selected from the group consisting of methoxy, ethoxy, propyloxy, and butyloxy; and
$R_2$ and $R_3$ are independently selected from hydrogen, hydroxy, methoxy, ethoxy, propoxy, butoxy, dimethylamino, diethylamino, dipropylamino, and dibutylamino.

* * * * *